(12) United States Patent
Sun et al.

(10) Patent No.: US 11,344,601 B2
(45) Date of Patent: May 31, 2022

(54) TUMOR MICROENVIRONMENT-RELATED TARGET TAK1 AND APPLICATION THEREOF IN INHIBITION OF TUMOR

(71) Applicant: Shanghai Institutes for Biological Sciences, Chinese Academy of Sciences, Shanghai (CN)

(72) Inventors: Yu Sun, Shanghai (CN); Boyi Zhang, Shanghai (CN)

(73) Assignee: Shanghai Institute of Nutrition and Health, Chinese Academy of Sciences, Shanghai (CN)

(*) Notice: Subject to any disclaimer, the term of this patent is extended or adjusted under 35 U.S.C. 154(b) by 115 days.

(21) Appl. No.: 16/640,826

(22) PCT Filed: Aug. 17, 2018

(86) PCT No.: PCT/CN2018/101003
§ 371 (c)(1),
(2) Date: Feb. 21, 2020

(87) PCT Pub. No.: WO2019/037658
PCT Pub. Date: Feb. 28, 2019

(65) Prior Publication Data
US 2021/0030836 A1 Feb. 4, 2021

(30) Foreign Application Priority Data
Aug. 25, 2017 (CN) .......................... 201710741005.3

(51) Int. Cl.
| A61K 38/14 | (2006.01) |
| A61P 35/00 | (2006.01) |
| A61K 31/136 | (2006.01) |
| A61K 31/337 | (2006.01) |
| A61K 31/365 | (2006.01) |
| A61K 45/06 | (2006.01) |

(52) U.S. Cl.
CPC ............ *A61K 38/14* (2013.01); *A61K 31/136* (2013.01); *A61K 31/337* (2013.01); *A61K 31/365* (2013.01); *A61P 35/00* (2018.01); *A61K 45/06* (2013.01)

(58) Field of Classification Search
CPC .. A61K 31/395; A61K 31/136; A61K 31/337; A61K 31/365; A61P 35/00
See application file for complete search history.

(56) References Cited

FOREIGN PATENT DOCUMENTS

| CN | 1921864 A | 2/2007 |
| CN | 101490279 A | 7/2009 |
| WO | 2012166722 A1 | 12/2012 |

OTHER PUBLICATIONS

Melisi. JNCI, 2011, 103 (15), 1190-1204 (Year: 2011).*
Augeri et al. "Inhibition of B P and of TGFb receptors downregulates expression of XIAP and TAK1 leading to lung cancer cell death". Molecular Cancer (2016) 15:27.
Haidi et al "Influence on Silencing TAKI Expression by siRNA to Decrease Drug Resistance and Proliferation of Prostate Cancer Line DU145 Cells". World Sci-Tech R&D vol. 36, No. 4, Aug. 2014, pp. 402-406.
Wang et al. "TAKI inhibitor NG25 enhances doxorubicin-mediated apoptosis in breast cancer cells" Science Reports, 6:32737.
Han et al. "Autophagy Inhibition Can Overcome Radoresistance in Breast Cancer Cells Through Suppression of nTAK1 Activation". Anticancer Research 34: 1449-1456, (2014).

* cited by examiner

*Primary Examiner* — Noble E Jarrell
(74) *Attorney, Agent, or Firm* — Banner & Witcoff, Ltd.

(57) ABSTRACT

Disclosed are a novel tumor microenvironment-related target TAK1 and an application thereof in inhibition of a tumor. TAK1, as a research target for SASP regulation, can be used as a marker in tumor diagnosis and prognosis, and can also be used as a tumor microenvironment specific target to develop tumor inhibitory drugs.

5 Claims, 11 Drawing Sheets
(10 of 11 Drawing Sheet(s) Filed in Color)
Specification includes a Sequence Listing.

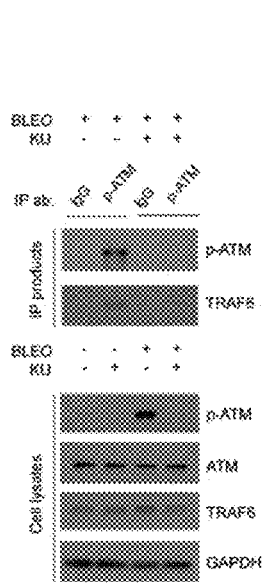
Figure 1
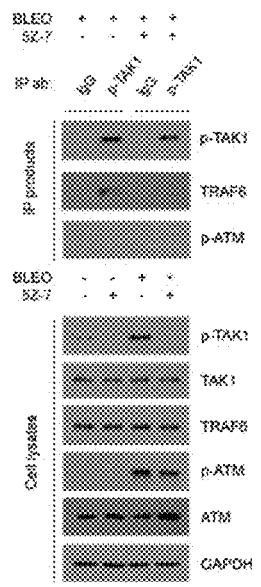
Figure 2
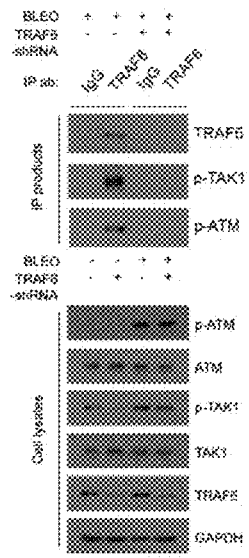
Figure 3
Figure 4
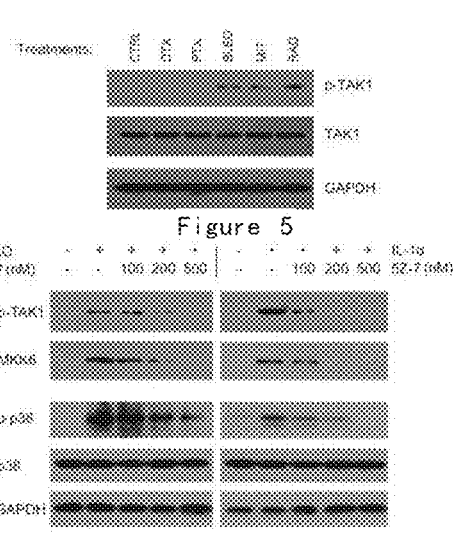
Figure 5
Figure 6
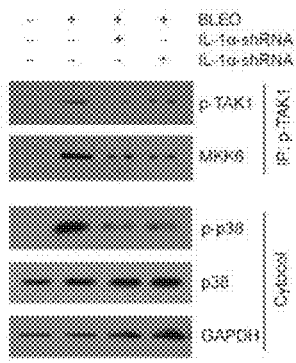
Figure 7
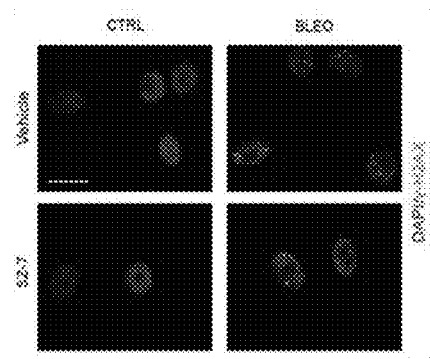
Figure 8

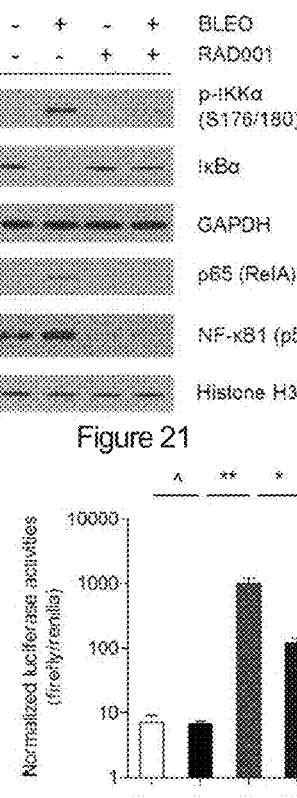
Figure 21
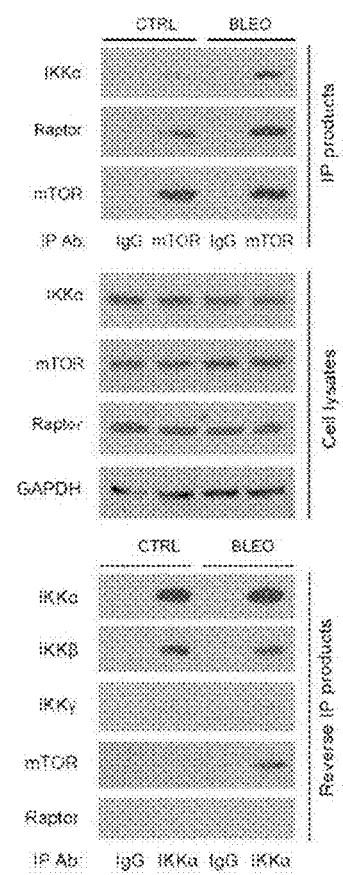
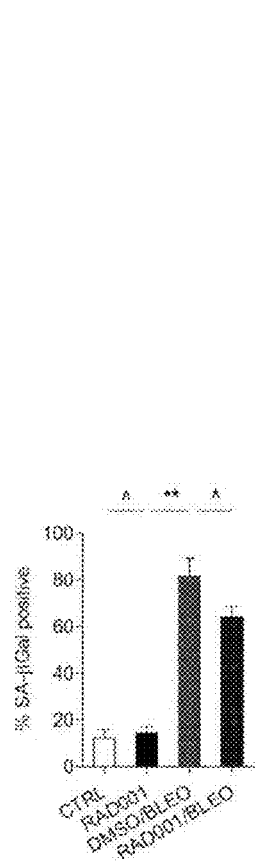
Figure 20
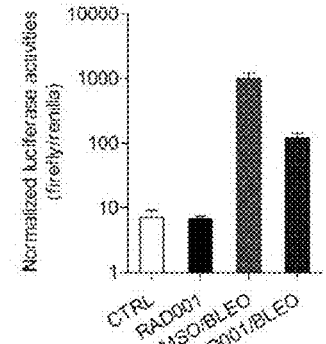
Figure 22
Figure 23
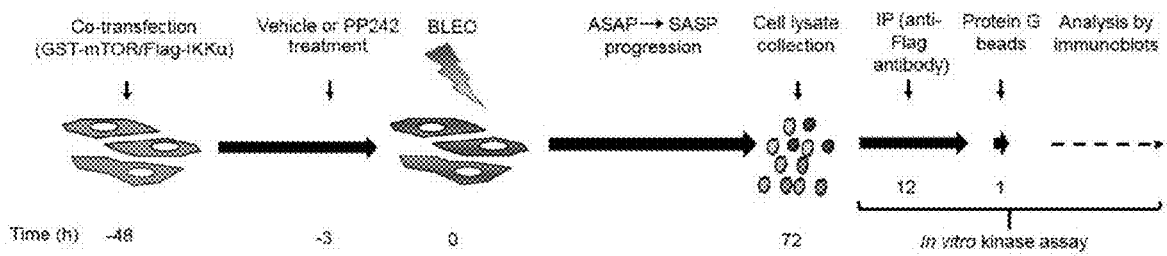
Figure 24
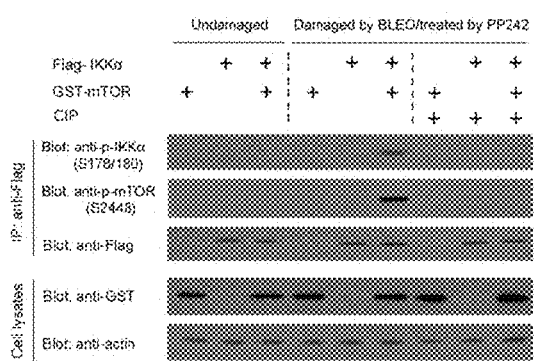
Figure 25
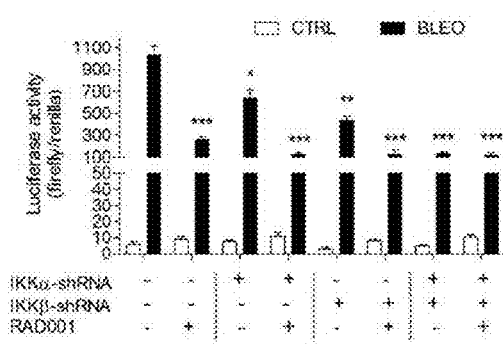
Figure 26

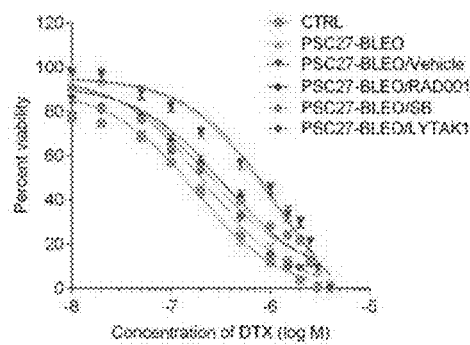
Figure 61
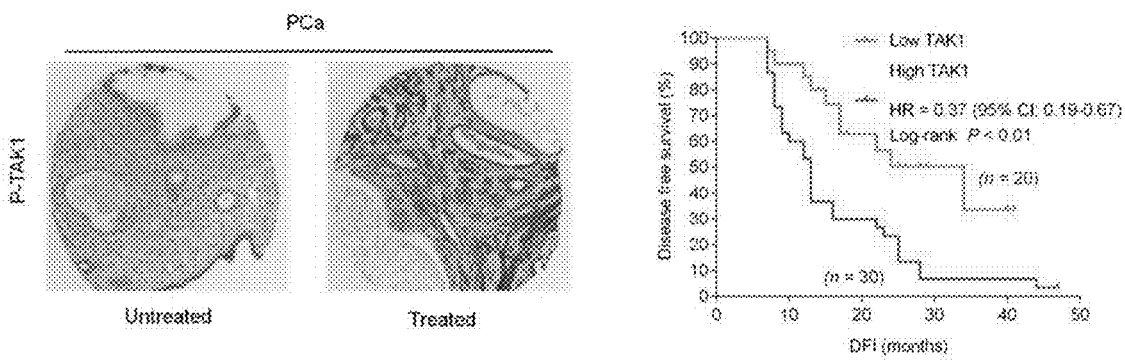
Figure 62
Figure 63
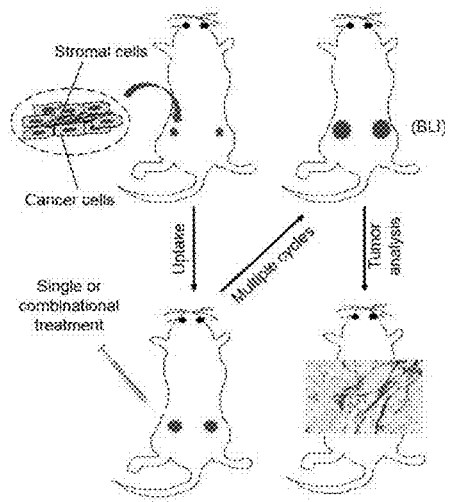
Figure 64

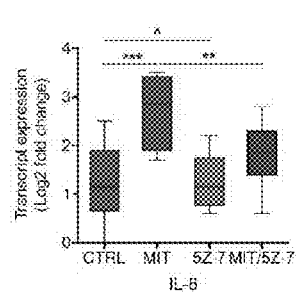
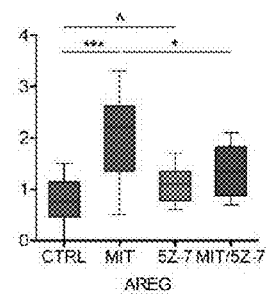
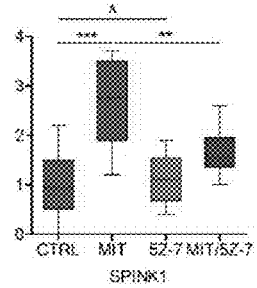
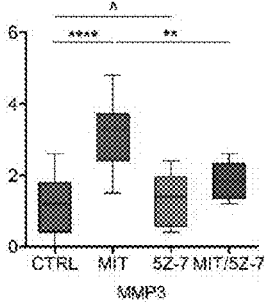
Figure 71     Figure 72     Figure 73     Figure 74
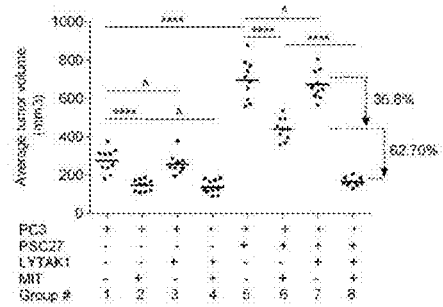
Figure 75
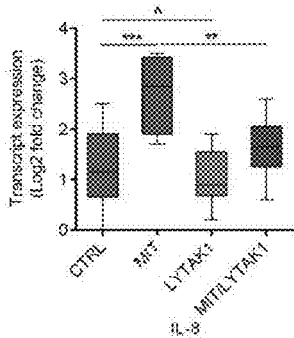
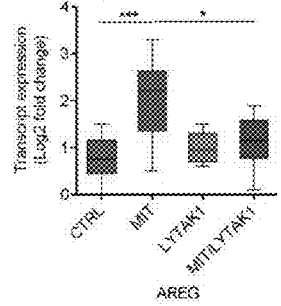
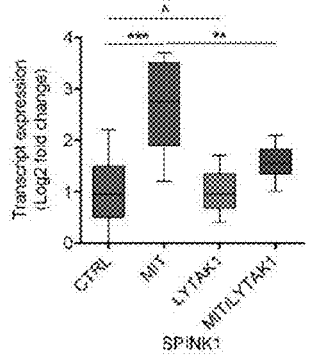
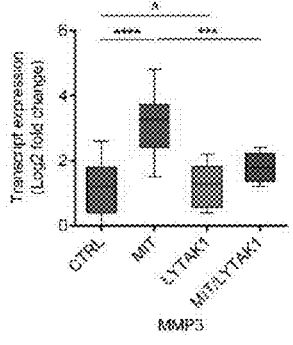
Figure 76     Figure 77     Figure 78     Figure 79
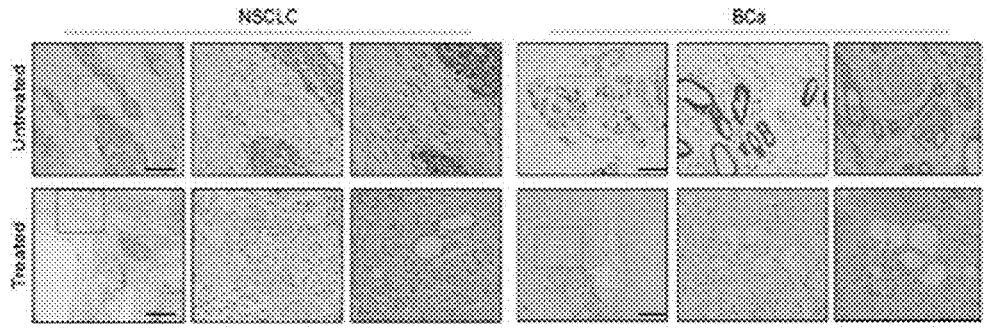
Figure 80

ID

SEQUENCE LISTING

<160> NUMBER OF SEQ ID NOS: 6

<210> SEQ ID NO 1
<211> LENGTH: 21
<212> TYPE: DNA
<213> ORGANISM: Artificial
<220> FEATURE:
<223> OTHER INFORMATION: Primer

<400> SEQUENCE: 1
gccacgggaa atatgtaata t                    21

```
<210> SEQ ID NO 2
<211> LENGTH: 21
<212> TYPE: DNA
<213> ORGANISM: Artificial
<220> FEATURE:
<223> OTHER INFORMATION: Primer

<400> SEQUENCE: 2
cggaatttcc aggaaactat t                                              21

<210> SEQ ID NO 3
<211> LENGTH: 21
<212> TYPE: DNA
<213> ORGANISM: Artificial
<220> FEATURE:
<223> OTHER INFORMATION: Primer

<400> SEQUENCE: 3
cccgtgtgaa ccatcctaat a                                              21

<210> SEQ ID NO 4
<211> LENGTH: 21
<212> TYPE: DNA
<213> ORGANISM: Artificial
<220> FEATURE:
<223> OTHER INFORMATION: Primer

<400> SEQUENCE: 4
cgcccttcaa tggaggaaat t                                              21

<210> SEQ ID NO 5
<211> LENGTH: 21
<212> TYPE: DNA
<213> ORGANISM: Artificial
<220> FEATURE:
<223> OTHER INFORMATION: Primer

<400> SEQUENCE: 5
gccaaagttc cagacatgtt t                                              21

<210> SEQ ID NO 6
<211> LENGTH: 21
<212> TYPE: DNA
<213> ORGANISM: Artificial
<220> FEATURE:
<223> OTHER INFORMATION: Primer

<400> SEQUENCE: 6
gaatgacgcc ctcaatcaaa g                                              21
```

TUMOR MICROENVIRONMENT-RELATED TARGET TAK1 AND APPLICATION THEREOF IN INHIBITION OF TUMOR

RELATED APPLICATION DATA

This application is a National Stage Application under 35 U.S.C. 371 of co-pending PCT application number PCT/CN2018/101003 designating the United States and filed Aug. 17, 2018; which claims the benefit of CN application number 201710741005.3 and filed Aug. 25, 2017 each of which are hereby incorporated by reference in their entireties.

TECHNICAL FIELD

The invention belongs to the field of pharmacy. More specifically, the invention involves a novel tumor-associated target TAK1 and its application in inhibition of a tumor.

BACKGROUND TECHNIQUES

1. Senescence and Senescence-Associated Secretory Phenotype

Cellular senescence is a process in which cells enter a permanent cell cycle arrest. Cellular senescence is often accompanied by a plurality of pathological features, including local inflammation. Cellular senescence occurs in damaged cells and prevents their proliferation in organisms. Under the influence of various external stimuli and internal factors, cell damage can elicit obvious signs of cellular senescence; when the damage accumulates and reaches a certain level, the tissue displays various symptoms of degeneration and physiological aging phenotypes that can be observed by naked eye.

The concept of senescence-associated secretory phenotype (SASP) was first proposed by Coppe et. al. in 2008. They found that senescent cells promote carcinogenesis in neighboring pre-cancerous cells by secreting extracellular matrix proteins, inflammation associated factors and growth factors, which were together termed as SASP factors. Under in vivo conditions, senescent cells accumulate in various organs, accompanied by production of a series of SASP factors. It is a phenotype characterized by significantly enhanced intracellular expression and extracellular release of different kinds of cytokines, and is an important biochemical and cytological feature of senescent cells. SASP includes pro-inflammatory cytokines (e.g. IL-1α, IL-1β, IL-6 and IL-8), growth factors (e.g. HGF, TGF-β and GM-CSF), chemokines (e.g., CXCL1/3 and CXCL10), and matrix remodeling enzymes (e.g. MMP1 and MMP3), etc. The different biological activities induced by the components of SASP indicates that it interacts with other cells and constitutes a special multi-ligand and multi-receptor signaling mechanism to regulate the local environment of the tissue, and has the potential to cause or exacerbate malignant pathological conditions such as age-related disorders including cancer.

2. Molecular Mechanisms and Drug Regulation of SASP

Recent studies have shown that some physicochemical factors or biological stimuli can upregulate the synthesis and secretion of cellular SASP factor. SASP also occurs in narrow stromal vascular cells treated with LPS, which increases the expression of TNF-α, IL-1β, IL-6, MCP-1 and VEGF. HuR not only regulates replication longevity, but also modulates the expression of SASP-related cytokines in mouse fibroblasts, while RNAi-mediated HuR inhibition results in an increase in the expression of SASP-related cytokines. Mitochondrial dysfunction or activation of RAS in epithelial cells of adult Drosophila can lead to cellular senescence and SASP. PKCη promotes senescence by upregulating the expression of cell cycle inhibitors $p21^{CIP1}$ and $p27^{KIP1}$ and enhancing the transcription and secretion of IL-6, whereas the expression of IL-8 is specifically inhibited by PKCη.

The vast majority of the SASP-based data reported so far are related to the promotion of chronic inflammation, paracrine-related aging and accelerated progression of malignant tumors, while there are few studies on how to inhibit the development and secretion of SASP and to delay aging and age-related diseases.

TNF-α is the main component of SASP in some cell types. The biotherapeutic drug Adalimumab is a monoclonal antibody that can directly inhibit TNF-α. It can reduce the secretion of the SASP and significantly decrease the amount of released IL-6, while the expression levels of eNOS and miR-126-3p are significantly increased. Adamumab can also induce epigenetic modification of senescent cells, thereby reducing the cancer-promoting effect of SASP.

Certain specific flavonoids can suppress the SASP occurrence, partially related to the NF-κB subunit p65 and the IκBζ signaling pathway, and effectively protect from or alleviate chronic low-grade inflammation in degenerative pathologies such as cardiovascular disease and advanced cancer. Natural flavonoids such as Aacumin and Kaempferol strongly inhibit the SASP expression. These flavonoids upregulate IκBζ expression through the signaling pathway of IRAK1/IκBα, thereby inhibiting the activity of NF-κB subunit p65. Conversely, inhibition of IκBζ expression would increase SASP expression. In vivo experiments, oral Abutin significantly reduced SASP in the renal of older rats, an effect strongly associated with elevated levels of IκBζ mRNA.

In recent years, it has been found that JAK inhibitors can decrease the secretion of adipose precursor cells and umbilical vein endothelial cells (HUVEC) SASP, so the JAK pathway may be a potential target against age-related dysfunction. TRIM28 positively regulates the components of IL-6, IL-8, and other SASP factors, whereas the secretory phenotype is strongly inhibited when TRIM28 is depleted.

Recent data suggest that the mTOR inhibitor rapamycin can be an effective SASP inhibitor. mTOR controls SASP by regulating the translation of IL-1α and MAPKAPK2. In turn, the p38 downstream signal MAPKAPK2 phosphorylates RNA-binding protein ZFP36L1, thereby prevents the degradation of SASP factor transcripts. When mTOR is inhibited by drugs, ZFP36L1 is dephosphorylated, leading to the degradation of SASP transcripts and the abrogation of IL-1α feedback loop. Thus, small molecule inhibitors of p38MAPK and MK2 can inhibit SASP from human fibroblasts. Rapamycin reduces the mRNA levels of IL-6 and other cytokines, and selectively inhibits the translation of the membrane-bound cytokine IL-1α. Decreased secretion of IL-1α also reduces the stimulation of NF-κB transcriptional activity, while NF-κB has more regulatory effects on the SASP, revealing the anti-aging effect of the mTOR inhibitor rapamycin. Meanwhile, rapamycin can inhibit the ability of senescent fibroblasts to stimulate the growth of prostate tumors in mice. Therefore, rapamycin may ameliorate age-related diseases including advanced cancer, by suppressing age-related inflammation.

Cellular senescence is an effective anticancer mechanism that prevents the proliferation of mitotic competent cells and thus circumvents malignant transformation. Aging-promoting therapy has recently emerged as a new treatment for cancer, but this concept conflicts with SASP of senescent cancer cells, which promote tumor progression despite the effect of suppressing carcinogenesis by senescent cells. Activation of the JAK2/Stat3 pathway in prostate cancer cells with PTEN deletion establishes an immunosuppressive tumor microenvironment that leads to tumor growth and drug resistance development. Activation of the JAK2/Stat3 signaling pathway in Pten$^{-/-}$ tumors by downregulating the protein tyrosine phosphatase PTPN1/SHP2 provides evidence for the existence of a new PTEN/SHP2 axis. More importantly, the use of polyene paclitaxel in combination with JAK2 inhibitors in Pten$^{-/-}$ tumors would alter the SASP and improve the efficiency of polyene paclitaxel-induced senescence. These findings suggest that immune surveillance of senescent tumor cells can be suppressed in a specific genetic context, but may also be activated by drug therapy. The exocrine protein function produced by senescent cells often depends on the genetic background of senescent cancer cells. Although SASP is important for tumor biology, how it regulates tumors remains unclear.

SUMMARY OF INVENTION

The object of the invention is to provide a new target of tumor microenvironment, TAK1, and its application in inhibition of a tumor.

In the first aspect of the invention, use of a downregulator of TAK1 gene or protein in the preparation of a pharmaceutical composition for inhibition of a tumor is provided, the tumor is selected from the group consisting of prostate cancer, breast cancer and lung cancer.

In a preferred example, the tumor is a chemotherapeutics- or radiotherapy (or ionizing radiation)-treated tumor, or the tumor is aTAK1-expressing tumor.

In another preferred example, the chemotherapeutics include, but not limited to bleomycin, mitoxantrone, docetaxel, and paclitaxel.

In another preferred example, the pharmaceutical composition is used in combination with chemotherapeutics to inhibit tumor.

In another preferred example, the downregulator is selected from the group consisting of small molecular compounds that specifically inhibit TAK1; interference molecules that specifically interfere with the expression of TAK1 gene; or gene editing reagents that specifically knock out TAK1 gene (such as sgRNA that targets TAK1 gene); or antibodies or ligands that specifically bind to the protein encoded by TAK1 gene.

In another preferred example, the downregulator is a small molecular compound that specifically inhibits TAK1 selected from the group consisting of 5z-7-oxozeaenol (i.e., 5Z-7) or LYTAK1.

In another aspect of the present invention, use of TAK1 gene or protein in the preparation of a composition for regulating senescence-associated secretory phenotype (SASP); or in the preparation of a pharmaceutical composition for suppression of aging-related diseases.

In a preferred example, said aging-related diseases include: atherosclerosis, osteoarthritis, osteoporosis and other organ degenerative diseases.

In another aspect of the invention, a method for screening a potential substance that inhibits tumors is provided, the method comprises: (1) treating a system for expressing TAK1 gene with a candidate substance; and (2) detecting the expression or activity of TAK1 gene in the system, wherein, if the candidate substance can reduce the expression or activity of TAK1 gene, it indicates that the candidate substance is a potential substance that inhibits a tumor.

In a preferred example, step (1) includes: adding a candidate substance to a system for expressing TAK1 in a test group; and/or step (2) includes testing the expression or activity of TAK1 in the system of the test group and comparing it with a control group, wherein the control group is a system for expressing TAK1 without the candidate substance; If the expression or activity of TAK1 in the test group was statistically lower than that in the control group, it indicates that the candidate substance is a potential substance that inhibit a tumor.

In another preferred example, the system is selected from the group consisting of a cell system (such as cell or cell culture that expresses TAK1), a subcellular system, a solution system, a tissue system, an organ system or an animal system.

In another preferred example, the statistically lower than is preferably significantly lower than, such as lower than 20%, more preferably lower than 50%, and even preferably lower than 80%.

In another preferred example, the candidate substance includes, but not limited to small molecular compounds designed for TAK1 gene or protein, interference molecules designed for signaling pathways involved by TAK1 gene or protein or their upstream or downstream proteins, nucleic acid inhibitors, binding molecules (such as antibodies or ligands), etc.

In another preferred example, the method further comprises conducting further cell experiments and/or animal tests on the obtained potential substances to further select and identify a substance for inhibition of a tumor from the candidate substances.

In another aspect of the present invention, a pharmaceutical composition for inhibition of a tumor is provided. The pharmaceutical composition comprises a downregulation of TAK1 gene or protein, and chemotherapeutics or radiotherapy (ionizing radiation) therapeutics.

In another aspect of the invention, a kit for inhibition of a tumor is provided, the kit comprises:

Container 1, and a downregulation of TAK1 gene or protein packaged in container 1; and Container 2, and chemotherapeutics or radiotherapy (ionizing radiation) drugs packaged in container 2.

In a preferred example, the downregulators includes small molecular compounds that specifically inhibit TAK1, interference molecules that specifically interfere with the expression of TAK1 gene, or gene editing reagents that specifically knock out TAK1 gene (e.g., sgRNAs that target TAK1 gene), or antibodies or ligands that specifically bind to the protein encoded by TAK1 gene.

In another preferred example, the chemotherapeutics include, but not limited to bleomycin, mitoxantrone, docetaxel and paclitaxel.

In another aspect of the present invention, use of a reagent that specifically recognizes TAK1 gene or a protein it encodes in the preparation of a reagent or kit for tumor prognosis evaluation is provided.

In a preferred example, the reagent that specifically recognizes TAK1 gene or a protein it encodes is selected from the group consisting of primers that specifically amplify TAK1 gene, probes that specifically recognize TAK1 gene, or antibodies or ligands that specifically bind a protein encoded by TAK1 gene.

In another aspect of the present invention, a kit for tumor prognosis evaluation is provided, the kit contains reagents that specifically recognize TAK1 gene or a protein it encodes.

Other aspects of the invention are obvious to those skilled in the art based on the disclosure herein.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 1. Phosphorylated ATM (p-ATM) antibody-mediated IP analysis. The expression levels of TRAF6, p-ATM and ATM in IP precipitates were detected by Western blot. TRAF6, a loading control. PSC27 was treated with bleomycin (50 ug/ml) and then with the ATM small molecule inhibitor KU55933 (KU, 10 μM).

FIG. 2. After treatment of PSC27 cells with bleomycin along with 5Z-7 (500 nM) and anti-TAK1-mediated IP precipitation, the expression levels of p-TAK1, TRAF6, p-ATM in IP products and in cell lysates were analyzed by Western blot.

FIG. 3. PSC27 cells in the control group and TRAF6-specific shRNA stable transfected lines were treated with bleomycin followed by anti-TRAF6-mediated IP, the product was subjected to Western blot to analyze the post-translational modification level of each major protein, and the analysis in cell lysates was performed simultaneously.

FIG. 4. Cytosolic and nuclear proteins were specifically isolated and extracted by a kit after bleomycin treatment of stromal cells. The activation of ATM and TAK1, and NF-κB nuclear translocation were analyzed. Control cells and cells treated with 5Z-7 were analyzed in parallel.

FIG. 5. Treatment of PSC27 cells with different chemotherapeutics frequently used in clinics and radiation. The lysates of the damaged cells were collected and analyzed by Western blot for p-TAK1 expression levels, with total TAK1 and GAPDH as loading controls.

FIG. 6. In the presence of the TAK1 inhibitor 5Z-7, PSC27 cells were treated with bleomycin and cell lysates were subject to anti-p-TAK1-mediated IP precipitation. IP products were analyzed by in vitro kinase assay, and MKK6 was used as TAK1 substrate. p38 phosphorylation was analyzed by Western blot with GAPDH as the loading control. In addition, IL-1α (20 ng/ml) was used to treat stromal cells and was further analyzed by similar IP and in vitro kinase assay. Rad in this figure refers to radiation treatment (γ-radiation at 743 rad/min).

FIG. 7. PSC27 cells underwent shRNA-mediated IL-1α knockout, and p-TAK1-mediated IP, and subsequent Western blot analysis.

FIG. 8. Immunofluorescence staining analysis (γ-H2AX antibody) of DNA damage repair. Scale bar, 10 μm. Lower part, statistical analysis of results.

FIG. 20. Statistical comparative analysis of SA-B-Gal staining of each group of cells in FIG. 19.

FIG. 21. After the stromal cells were treated with bleomycin and/or RAD001, cells were collected on Day 7 and their NF-κB complex activation was measured. GAPDH and Histone H3 were cytoplasmic and nuclear protein loading controls, respectively.

FIG. 22. The stromal cells pre-transduced with the NF-κB transcriptional luciferase reporter vector were treated with bleomycin and/or RAD001. The cells were collected on Day 7 and detected for the fluorescence signal intensity of the reporter vector.

FIG. 23. After the stromal cells were treated with bleomycin and/or RAD001, cells were collected on Day 7 and the interaction between of mTOR and subunits of IKK complexes was analyzed by immunoprecipitation method. IgG, control antibody.

FIG. 24. Experimental flow of drug-treatment and in vitro kinase assay of stromal cells under in vitro conditions.

FIG. 25. Stromal cells were treated experimentally according to the sequence in FIG. 24, and then subjected to anti-flag-mediated IP precipitation. The expression of p-IKKα and p-mTOR was analyzed by Western blot to determine their physical interaction.

FIG. 26. After shRNA-mediated specific knockout of subunits a and p of the IKK complex, the stromal cells were then treated with bleomycin and/or RAD001 to analyze the signal intensity of their NF-κB transcriptional luciferase reporter vector.

FIG. 61. The survival rate of PC3 cells treated with extracellular fluids of PSC27 produced under several conditions, in the presence of different concentrations of docetaxel, compared to that of the untreated control group. Dose response curve, nonlinear regression.

FIG. 62. Change of the phosphorylation level (activation) of TAK1 in tissues of prostate cancer (PCa) clinical patients before and after chemotherapy analyzed by histochemical staining. The selected samples (left and right) were representative tissues before and after chemotherapy, respectively.

FIG. 63. Statistical analysis of PCa patient survival based on TAK1 activation. The number of patients with low expression of p-TAK1 was 20 and that of the high expression group was 30.

FIG. 64. Experimental flowchart of subcutaneously inoculating mice with cancer cells and/or stromal cells in a preclinical trial, followed by chemotherapy drug treatment and pathological analysis.

FIG. 71. Parallel comparison of transcript expression levels of chemokine IL-8 among groups of mouse tumors subjected to laser capture microdissection.

FIG. 72. Parallel comparison of transcript expression levels of extracellular factor AREG among groups of mouse tumors subjected to lase capture microdissection.

FIG. 73. Parallel comparison of transcript expression levels of growth factor SPINK1 among groups of mouse tumors subjected to laser capture microdissection.

FIG. 74. Parallel comparison of transcript expression levels of extracellular matrix metalloproteinase MMP3 among groups of mouse tumors subject to laser capture microdissection.

FIG. 75. Statistical comparative analysis of mouse terminal tumor volume (LYTAK1 instead of 5Z-7 administration). Compared with group 5, the volume of group 6 decreased by 37%; compared with group 6, the volume of group 8 decreased by 63%.

FIG. 76. Parallel comparison of transcript levels of chemokine IL-8 in mouse tumors (including the LYTAK1 administration group) among groups of mouse tumors subject to laser capture microdissection.

FIG. 77. Parallel comparison of transcript expression levels of extracellular factor AREG (including the LYTAK1 administration group) among groups of mouse tumors subject to laser capture microdissection.

FIG. 78. Parallel comparison of transcript expression levels of growth factor SPINK1 (including the LYTAK1 administration group) among groups of mouse tumors subjected to laser capture microdissection.

FIG. 79. Parallel comparison of transcript expression levels of extracellular matrix metalloproteinase MMP3 (including the LYTAK1 administration group) among groups of mouse tumors subject to laser capture microdissection.

FIG. 80. IHC and pathological analysis of in situ tumor tissues in patients with clinical NSCLC and BCa. In each cancer type, the upper group represent samples without chemotherapy, while the lower group represents patient tissues subject to chemotherapy. The left sample was the IHC staining result based on p-TAK1, with the selected area of the red box enlarged in the middle, while the right side was the corresponding HE staining result of the middle tissue.

DETAILED DESCRIPTION

Figure 9:
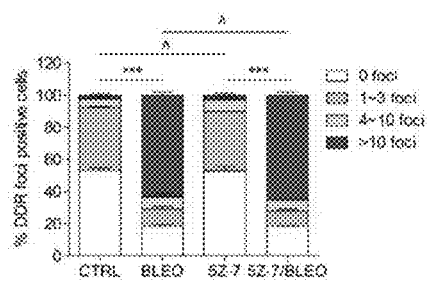
FIG. 9. Comparative analysis of the statistical results of cell staining in each group of FIG. 8.

After extensive and in-depth research, the inventor reveals for the first time that TAK1 may play an important biological role in development of SASP phenotype, and it is also closely related to tumor development. Therefore, TAK1 can be used as a research target for the regulation of SASP phenotype, as a diagnostic, prognostic evaluation marker for tumor, and as a target for the development of drugs to inhibit a tumor.

TAK1

Transforming growth factor kinase 1 (TAK1) has a Gene ID of 6885 in GenBank, encoding a protein of 606 amino acids.

TAK1 is a member of the mitogen-activated protein 3 kinase (MAP3K) family and is functionally located upstream of mitogen protein kinase (MAPK) and IκB kinase. It can be activated by a variety of cytokines, including IL-1, involving in many important physiological processes in body, and by co-expression with a binding protein, TAB1. Phosphorylation modification is considered to be an important regulatory mechanism in TAK1-dependent signaling process, but the regulatory phosphorylation sites of TAK1 protein are not fully identified. The activation mechanism of TAK1 at the molecular level is also not fully elucidated.

The present inventor finds that the ATM-TRAF6-TAK1 signaling axis regulates NF-κB complex activation in acute responses triggered by DNA damage in stromal cells, which is closely related to the expression of chronic SASP downstream effectors. TAK1 mediates activation of p38MAPK signaling pathway upon DNA damage, but drug inhibition against its kinase activity does not affect DNA damage response and stromal cell proliferation potential. Moreover, the mTOR pathway downstream of TAK1 plays an important role in the development of the chronic phase of SASP.

The present inventor also finds that inhibition of TAK1 can reverse multiple malignant phenotypes conferred on cancer cells by damaged stromal cells in vitro. Targeting TAK1 can effectively restore tumor sensitivity to chemotherapeutics by interfering with development of SASP of stromal cells in microenvironment. However, the TAK1 downregulator alone has no significant effect on tumor growth. Co-administration with conventional chemotherapeutics can cause a significant decrease in tumor volume by blocking the SASP secretory phenotype in the microenvironment, thus representing an example of novel use of old drugs.

Those skilled in the art would understand that cellular senescence is often accompanied by the occurrence of the senescence-associated secretory phenotype (SASP). Given the close association of TAK1 with SASP TAK1 is known to be a new target for SASP to research, develop, or prepare pharmaceutical compositions that inhibit aging-related diseases. In a preferred embodiment, the aging-related diseases include atherosclerosis, osteoarthritis, osteoporosis, and other organ degenerative diseases.

TAK1 Downregulator

Based on the above new discovery by the inventor, the invention provides use of a downregulator of TAK1 gene or protein in the preparation of a pharmaceutical composition for inhibition of a tumor. The tumors are selected from the group consisting of tumors treated with chemotherapeutic or radiotherapy, or the tumors are tumors wherein stromal cells express TAK1. The chemotherapeutics treatment or radiation includes: docetaxel, paclitaxel, bleomycin, mitoxantrone, radiotherapy rays, etc.

As used herein, the downregulator of TAK1 gene or protein includes inhibitors, antagonists, blockers, suppressors, etc.

The downregulator of TAK1 gene or protein refers to any substance that can reduce the activity of TAK1 protein, reduce the stability of TAK1 gene or protein, downregulate the expression of TAK1 protein, reduce the effective time of TAK1 protein, or inhibit the transcription and translation of TAK1 gene. These substances can be used in the present invention as useful substances for downregulating TAK1, and thus can be used to inhibit a tumor. For example, the downregulators are interfering RNA molecules or antisense nucleotides that specifically interfere with the expression of TAK1 gene, or antibodies or ligands that specifically bind to the protein encoded by TAK1 gene, etc.

As an option for the invention, the downregulator is a small molecular compound against TAK1. Those skilled in the art can screen such small molecular compounds with conventional screening method in the art. For example, the small molecular compound is 5z-7-oxozeaenol (5Z-7) or LYTAK1.

As an option for the invention, the downregulator is a TAK-specific interfering RNA molecule (shRNA). The inventor observed that TAK1 may be significantly downregulated using the interfering RNA molecule of the invention, and the inhibitory effect on tumor is significant.

The invention has no special limitations on the preparation method of interfering RNA molecules, including but not limited to chemical synthesis, in vitro transcription, etc. The interfering RNA may be delivered to cells with an appropriate transfection reagent, or with a variety of techniques known in the art.

As another option for the present invention, targeting-gene editing can be performed using the CRISPR/CAS9 system to knock out TAK1 gene in the targeted region of a disease. Common methods for knocking outTAK1 gene comprise co-transferring sgRNA or nucleic acid that can form the sgRNA, Cas9 mRNA or nucleic acid that can form the Cas9 mRNA to target regions or target cells. After identifying the target site, a known method can be used to introduce sgRNA and Cas9 into cells. The nucleic acids that can form the sgRNA are nucleic acid constructs or expression vectors, or the nucleic acids that can form the Cas9 mRNA are nucleic acid constructs or expression vectors, and these vectors are introduced into cells to form active sgRNA and Cas9 mRNA within cells.

Reagents or Kits for Tumor Prognosis Evaluation

Based on the inventor's new findings, TAK1 may be used as a marker for tumor prognosis evaluation: (i) typing, differential diagnosis, and/or susceptibility analysis of tumors; and (ii) evaluation of tumor therapy drugs, drug efficacy, prognosis, and selection of appropriate therapies for the population concerned. For example, a population with abnormal TAK1 gene expression can be isolated and treated more specifically.

According to the new findings of the inventor, the tumor prognosis of the subjects from which a sample to be evaluated is provided can be predicted by determining the expression or activity of TAK1 in the sample to be evaluated, and the appropriate drugs can be selected for treatment. Typically, a threshold of TAK1 can be specified. When the expression of TAK1 is above the threshold, it is considered to use a regimen of TAK1 inhibition for treatment. The threshold of abnormal expression of TAK1 is easy to determine for those skilled in the art, for example, by comparing the expression of TAK1 in normal human tissue microenvironment with that in tumor patient microenvironment.

Therefore, the present invention provides use of TAK1 gene or protein in preparation of a reagent or kit for tumor prognosis evaluation.

The presence and expression of TAK1 gene may be detected with various known techniques in the art, which are included in the present invention. For example, known techniques such as Southern blot, Western blot, DNA sequence analysis, PCR and so on can be used in combination.

The invention also provides a reagent for detecting the presence and expression of TAK1 gene in analytes. Preferably, when testing in gene level, primers for specific amplification of TAK1 or probes for specific identification of TAK1 can be used to determine the presence or absence of TAK1 gene. When testing in the protein level, antibodies or ligands that specifically bind TAK1-encoded proteins can be used to determine the expression of TAK1 protein.

The design of specific probes for TAK1 gene is a well-known technique in the art. For example, a probe is prepared, which can specifically bind to specific sites on TAK1 gene without specific binding to genes other than TAK1 gene, and the probe has a detectable signal.

It is a well-known technique in the art to use antibodies that specifically bind TAK1 protein to detect the expression of TAK1 protein in analytes.

The invention also provides a kit for detecting the presence and expression of TAK1 gene in analytes. The kit includes primers that specifically amplify TAK1 gene, probes that specifically recognize TAK1 gene, or antibodies or ligands that specifically bind to the protein encoded by TAK1 gene.

In addition, the kit may include various reagents needed for extracting DNA, PCR, hybridization, color rendering, etc. These reagents include but not limited to extract solution, amplification solution, hybridization solution, enzyme, control solution, development solution, lotion, etc.

In addition, the kit may include use instructions and/or software for nucleic acid sequence analysis, etc.

Drug Screening

Based on the knowledge that overexpression of TAK1 promotes the growth of specific tumor cells and inhibition of TAK1 expression inhibits the growth of these tumor cells, one can screen substances that inhibit the expression or activity of TAK1 based on these performance. A truly useful drug for inhibition of a tumor can be found from the substances. Preferably, the specific tumors are selected from the group consisting of prostate cancer, breast cancer and lung cancer.

Thus, the invention provides a method for screening a potential substance for inhibition of a tumor. The method comprises treating a TAK1 expressing system with a candidate substance; and detecting the expression or activity of TAK1 in the system; if the candidate substance can inhibit the expression or activity of TAK1, it indicates that the candidate substance is a potential substance for inhibition of a tumor. The TAK1-expressing system is preferably a cell (or cell culture) system. The cell may be a cell that expresses TAK1 endogenously, or a cell that expresses TAK1 recombinantly.

In a preferred embodiment of the invention, in order to observe the change of the expression or activity of TAK1 during screening more easily, a control group may also be set, wherein the control group may be a TAK1-expressing system with no candidate substances added.

In a preferred embodiment of the invention, the method also comprises conducting further cell experiments and/or animal tests on the obtained potential substances to further select and identify substances that are truly useful for inhibiting a tumor.

In another aspect, the invention also provides a potential substance for inhibition of a tumor obtained through using the screening method. These preliminarily screened substances can form a screening bank so that one can eventually screen for substances that are useful in inhibiting the expression and activity of TAK1 and, in turn, inhibiting a tumor.

Pharmaceutical Composition

The invention also provides a pharmaceutical composition containing an effective amount (e.g., 0.000001-50 wt %; better 0.00001-20 wt %; better, 0.0001-10 wt %) of the downregulators of TAK1 gene or protein, as well as a pharmaceutically acceptable carrier. Any downregulator of the aforementioned TAK1 gene or protein can be used for composition preparation.

In a preferred embodiment of the invention, a composition for inhibiting a tumor is provided. The composition contains an effective amount of the interference RNA molecule described herein, and a pharmaceutically acceptable carrier.

In a preferred embodiment of the invention, a composition for inhibition of a tumor is provided. The composition contains an effective amount of a downregulator of TAK1 gene or protein, and effective amounts of other formulations, such as genotoxic drug or DNA damaging drug, or ionizing radiation therapy agent.

As used herein, term "effective amount" refers to the amount that can be functional or active to humans and/or animals and acceptable to humans and/or animals. Term "pharmaceutically acceptable carrier" refers to the carrier used for therapeutic delivery, including various excipients and diluents. The term refers to a number of pharmaceutical carriers that are not essentially active components by themselves and are not overly toxic after application. Suitable carriers are well known to those skilled in the art. A pharmaceutically acceptable carrier in a composition may contain liquids such as water, saline, buffer. In addition, there may be auxiliary substances in these carriers, such as fillers, lubricants, glidants, wetting agents or emulsifiers, pH buffers, etc. The carrier may also contain a cell transfection reagent.

Having been informed of the use of a downregulator of TAK1 gene or protein, one may administrate the downregulator or its coding gene, or its pharmaceutical composition, to mammals using a plurality of well-known methods in the art, including but not limited to subcutaneous injection, intramuscular injection, percutaneous administration, local administration, implantation, sustained release, etc., preferably, the administration is non-intestinal.

Preferably, administration can be performed by means of gene therapy. For example, TAK1 downregulators can be administered directly to subjects through methods such as injection; or the expression units carrying TAK1 downregulators (e.g., expression vectors or viruses, or siRNAs) can be delivered to target sites in certain ways, and the expression of active TAK1 downregulator is allower, depending on the type of the downregulator, which is well known to those skilled in the art.

The effective amount of TAK1 gene or protein of the invention may vary with the mode of administration and the severity of the disease to be treated. The selection of a preferred effective amount can be determined by those skilled in the art based on various factors (e.g., through clinical trials). The factors include but not limited to pharmacokinetic parameters of the downregulator of TAK1 gene or protein, e.g., bioavailability, metabolism, half-life, etc., and the severity of the disease to be treated, the patient's weight, the patient's immune status, the route of administration, etc.

The invention is further illustrated below in conjunction with specific embodiments. It should be understood that these embodiments are only used to illustrate the invention, but not to limit the scope of the invention. Experimental methods that do not indicate specific conditions in the following embodiments are usually in accordance with conventional conditions such as J. Sambrook et al., Molecular Cloning a Laboratory Manual, 3rd edition, Science Press, conditions described in 2002, or as recommended by the manufacturer.

I. Materials and Methods

1. Cell Culture
   (1) Maintenance of Cell Lines
   Normal human prostate primary stromal cell line PSC27 (obtained from Fred Hutchinson Cancer Research Center, USA) proliferates and passages in PSCC complete medium. Benign prostate epithelial cell line, BPH1, and prostate cancer epithelial cell lines, M12, DU145, PC3, LNCaP and VCaP (from ATCC) were all maintained in RPMI-1640 supplemented with 5% FBS, cultured in an incubator under 37° C. and 5% $CO_2$.
   (2) Cryopreservation and Recovery
   a. Cryopreservation
   Cells in logarithmic growth phase were collected with 0.25% trypsin, centrifuged at 1000 rpm for 2 min, with the supernatant discarded and cells resuspended in fresh cryopreservation solution. Cells were packed in marked sterile cryopreservation tubes, then cooled down by gradient (4° c. for 10 min, −20° c. for 30 min, −80° c. for 16-18 h) and finally transferred to liquid nitrogen for medium- and long-term storage.
   b. Cell Recovery
   The frozen cells were taken out from liquid nitrogen and immediately put in 37° C. water bath to make it thawed quickly. 2 ml of cell culture medium was directly added to make the cells uniformly suspended. After the cells adhered to the wall, the culture medium was replaced with a new medium.
   c. Experimental Treatment In Vitro
   100 nM docetaxel (DTX), 100 nM paclitaxel (PTX), 200 nM vincristine (VCR), 50 μg/ml bleomycin (BLEO), 1 μM mitoxantrone (MIT), or 10 Gy $^{137}CS$ ionizing radiation (γ-radiation at 743 rad/min, RAD) was added to the culture medium when PSC27 cells grown to 80% (PSC27-Pre) to produce cell damage. After drug treatment for 6 hours, the cells were simply washed by PBS for 3 times and kept in the culture medium for 7 to 10 days, followed by subsequent experiments.
2. Plasmid Preparation and Lentiviral Transfection
   Full-length human IKKα and Flag were cloned as a fusion protein between the restriction sites BamHI and XbaI in the expression vector pCR3.1. Full-length human mTOR and GST were cloned as a fusion protein between a pair of NotI restriction sites in the expression vector pcDNA3. Packaging cell line 293FT was used for cell transfection and lentivirus production. The sequences of small hairpin RNAs (shRNAs) for knocking out TRAF6 were as follows:
   5'-gccacgggaaatatgtaatat-3'(SEQ ID NO: 1); and
   5'-cggaatttccaggaaactatt-3' (SEQ ID NO: 2).
   The sequences of small hairpin RNAs (shRNAs) for knocking out TAK1 were as follows:
   5'-cccgtgtgaaccatcctaata-3'(SEQ ID NO: 3); and
   5'-cgcccttcaatggaggaaatt-3'(SEQ ID NO: 4).
   The sequences of small hairpin RNAs (shRNAs) for knocking out IL-1α were as follows:
   5'-gccaaagttccagacatgttt-3'(SEQ ID NO: 5); and
   5'-gaatgacgccctcaatcaaag-3' (SEQ ID NO: 6).
3. Immunofluorescence and Histochemical Analysis
   Mouse monoclonal antibody anti-phospho-Histone H2A.X (Ser139) (clone JBW301, Millipore) or mouse monoclonal antibody anti-Phosphor-53BP1 (Cat #sc-135748, Santa Cruz), and secondary antibody Alexa Fluor® 488 (or 594)-conjugated F(ab')$_2$ were added sequentially to slides on which cells were fixed. Nuclei were counterstained with 2 μg/ml of 4',6-diamidino-2-phenylindole (DAPI). The most representative image was selected from the 3 observation fields for data analysis and result presentation. FV1000 laser scanning confocal microscopy (Olympus) was used to obtain cellular confocal fluorescence images to determine the extent of DNA damage.
   Antibody anti-TAK1 used for histological IHC staining in clinical prostate, non-small cell lung cancer patients and breast cancer patients, was purchased from Proteintech, idib. The specific steps were as follows: conventional dewaxing, incubating at 37° C. with 0.6% $H_2O_2$ methanol for 30 min, then retrieving with 0.01 M citrate buffer pH6.0 for 20 min and cooling at room temperature for 30 min. They were blocked with normal sheep serum for 20 min, incubated at 37° C. for 1 h with TAK1 primary antibody (1:200) and moved to a refrigerator at 4° C. overnight. The next day, slides was washed three times with TBS and incubated at 37° C. for 45 min with a secondary antibody (HRP-coupled goat anti-rabbit), then washed 3 times with TBS, and finally developed with DAB.
4. Stromal-Epithelial Co-Culture and In Vitro Experiments
   PSC27 cells were cultured with DMEM 0.5% FBS medium for 3 days and the cell population at full abundance were washed with 1×PBS. The supernatant was collected as conditioned medium for storage at −80° C. or direct use after simple centrifugation. Prostate epithelial cells were cultured in the conditioned medium for 3 days in vitro. For chemotherapy resistance, epithelial cell lines were cultured in low serum DMEM (0.5% FBS), or in conditioned medium, while mitoxantrone (MIT) was used to treat cells for 1 to 3 days at concentrations close to the IC50 values of each cell line, followed by observation under a brightfield microscope.
5. Genome-Wide Expression Analysis with Microarray (Agilent Expression Microarray)
   Procedures and methods for genome-wide expression chip (4×44k) analysis of the normal human prostate primary stromal cell line PSC27, can refer to Sun, Y. et al., Nat Med. 2012. 18: 1359-1368.
6. Quantitative PCR for Measuring Gene Expression
   (1) Extraction of Total RNA from Cells
   Total RNA of proliferating cells were extracted with Trizol reagent, with 1 ml of Trizol added per T25 culture flask. The cell layer was scraped off with a cell scraper, transferred to the centrifuge tube, and well mixed to non-sticky. For each 1 ml Trizol, 0.2 ml chloroform was added, rigorously shaken for 15 seconds, incubated at room temperature for 5-10 min, centrifuged at 4° C., 11,000 g for 15 min, with the colorless supernatant transferred to a new centrifuge tube. For each 1 ml Trizol, 0.5 ml isopropanol was added, incubated at room temperature for 10 min, centrifuged at 11,000 g, 4° C. for 10 min, with supernatant disposed, washed with 75% ethanol (at least 1 ml 75% ethanol per 1 ml Trizol), centrifuged at 4° C., 7,500 g for 5 min, with RNA dried at room temperature for 5-10 min (not dry) and precipitate dissolved with DEPC-$H_2O$.

After RNA quantitationRNA with a spectrophotometer, a small amount of total RNA was taken for 1% agarose electrophoresis to check the status and quality of RNA.

(2) Reverse Transcription

| OligodT$_{23}$ V$_N$ (50 uM) | 1 ul |
|---|---|
| Total RNA | 1-2 ug |
| RNase Free ddH$_2$O | to 8 ul |

Heated at 65° C. for 5 minutes, quickly placed on ice for sudden cooling and allowed to stand for 2 minutes.

The synthesis solution for first strand cDNA was prepared.

| 2 × RT Mix | 10 ul |
|---|---|
| HiScript II Enzyme Mix | 2 ul |

The synthesis of the first strand cDNA was performed as follows:

| 25° C. | 5 min |
|---|---|
| 50° C. | 45 min |
| 85° C. | 5 min |

(3) Real Time Quantitative PCR Reaction

The reverse transcription reaction product cDNA was diluted 50 times as a template.

| AceQ SYBR Green Master Mix | 10 ul |
|---|---|
| Primer 1 (10 uM) | 0.4 ul |
| Primer 2 (10 uM) | 0.4 ul |
| Rox Reference Dye | 0.4 ul |
| Template | 2 ul |
| ddH$_2$O | to 20 ul |

Loading according to above criteria, the reaction condition was as follows: pre-denaturation at 95° C. for 15 s, then 95° C. 5 s, 60° C. 31 s for 40 cycles; the melting curve condition was 95° C. 15 s, 60° C. 30 s, 95° C. 15 s. Samples were placed on ABI ViiA7(ABI) instrument for reaction. The expression of β-actin was used as internal reference. After the reaction was completed, the amplification of each gene was examined by software analysis, and the corresponding cycle number was exported. The 2-ΔΔCt method was used to calculate the relative expression of each gene. The peaks and waves of the melting curve were analyzed to determine whether the resulted amplification product was a specific single target fragment.

7. Western Blot Analysis (1) Total Protein Extraction

After cells were simply washed with ice-cold PBS buffer, the RIPA cell lysis buffer containing 1 mM PMSF (protease inhibitor) was added. The cells were placed on ice for 30 min. The cell lysates were collected with a cell scraper and centrifuged at 4° C. 12,000 rpm for 15 min. The supernatant was preserved at −80° C.

(2) Protein Quantitation with BCA Assay

With a BCA protein quantitation kit (pierce), the reagent A and reagent B were mixed in a ratio of 1:50 to make the working solution ready for use. The standard protein was diluted to a concentration of 0 μg/μl, 25 μg/μl, 50 μg/μl, 100 μg/μl, 250 μg/μl, 500 μg/μl, 750 μg/μl, 1000 μg/μl, and 2000 μg/μl. 5 μl standard protein or 5 μl sample was added to the microtiter plate, then 100 μl BCA working solution was added, and incubated in water bath at 37° C. for 30 min after mixing evenly. The absorbance value at 570 nm wavelength was measured with a microplate reader. The standard curve was plotted with the absorbance value as the vertical coordinate and the standard protein concentration as the horizontal coordinate. The concentration of the sample was calculated according to the standard curve.

(3) SDS-PAGE Electrophoresis

12% SDS-PAGE (5 ml system contained 30% acrylamide 2 ml, ddH$_2$O 1.6 ml, 1.5 M pH8.8 Tris-HCl 1.3 ml, 10% SDS 50 μl, 10% ammonium persulfate 50 μl, TEMED 2 μl) was prepared, mixed quickly, and then filled into the gaps of clean preset glass plate (Bio-Rad), and an appropriate amount of deionized water was added to the top layer to promote gel polymerization at room temperature for 30 min. After fully condensation, the upper layer of deionized water was discarded and residual liquid was absorbed with a filter paper. Stacking gel (2 ml system contained 30% acrylamide 0.33 ml, 1.0 M pH 6.8 Tris-HCl 0.25 ml, 10% SDS 20 μl, 10% ammonium persulfate 20 μl, TEMED 2 μl) was prepared, add the mixture immediately to the upper layer of the separation gel after mixing, with a clean 10 tooth comb inserted, set aside at room temperature for 30 min, with the comb removed after full condensation of the stacking gel, the loading slots were washed with ddH$_2$O for several times, and the gel was placed in the electrophoretic tank (Bio-Rad) and the electrophoretic buffer solution (containing 25 mm 8.0 Tris, 0.25 M Glycine, 0.1% SDS) was added. The protein samples were mixed with 6× loading buffer solution (containing 300 mM pH 6.8 Tris-HCl 12% SDS, 600 mM DTT, 60% glycerol, 0.6% bromophenol blue) at 5:1, boiled in water for 10 min, and cooled on ice for 5 min. According to protein quantitation results, an equal amount of protein sample was add in each lane, and subjected to electrophoresis with Bio-Rad electrophoresis instrument, wherein a 80V voltage was first applied for ~20 minutes to allow bromophenol blue to enter the front of separation gel, then the voltage was increased to 120V for about 1 hour until bromophenol blue reached the bottom of gel. Then electrophoresis was done.

(4) Protein Transmembrane

After SDS-PAGE electrophoresis, the stacking gel and no sample area were cut off, and the nitrocellulose membrane was briefly immersed in electrophoretic transfer buffer. Materials were placed on the electric transfer device (Bio-Rad) from anode to cathode in the order of Bio-Rad 3 mm filter paper, nitrocellulose filter membrane, gel, and Bio-Rad 3 mm filter paper. Electrical transfer was conducted at 100V voltage for 1.5 h. After the end of transmembrane, the transfer effect was determined by pre-straining marker and 0.1% Ponceau Stain, and decolorized by ddH$_2$O for 5 min.

(5) Antibody Labeling and ECL Detection

The nitrocellulose filter membrane was blocked at room temperature for 1 h in the blocking solution (TBST containing 5% skim milk powder (0.1% Tween-20 in TBS)), incubated overnight at 4° C. in a primary antibody solution, rinsed at TBST room temperature for 3 times, each for 2 min. The corresponding secondary antibody conjugated with HRP prepared with the blocking solution was added, the filter membrane was incubated at room temperature for 0.5 h. The filter membrane was rinsed with PBST at room temperature for 3 times, each for 2 min.

The equal ratio of substrate and enhancer of SuperSignal West Pico kit (Pierce) were mixed and added to the filter membrane dropwise evenly, incubated for 1 minute at room temperature, the x-ray films were after developed and fixied, scanned and analyzed.

8. Analysis of NF-κB Regulation

The antiviral vector pBABE-puro-IκBα-mut (Super repressor) containing two phosphorylated mutant sites of IKK at S32A and S34A on the IκBα protein encoding sequence were used for transfection of lentivirus-packing cell line phoenix. Lentiviruses were subsequently used to infect PSC27 stromal cell line, whereas 1 µg/ml puromycin was used to screen positive clones. As another method, 5 µm of the small molecule inhibitor Bay11-7082 (purchased from Selleck) was used for NF-κB activity control. Stromal cells were subsequently exposed to several different forms of cytotoxicity, with the resulting phenotype recorded in time, and the relevant gene expression analyzed. The resulted conditioned culture medium produced from cells processed in this way was collected for various detection of epithelial cells.

10. Collection and Analysis of Tissue Samples from Clinical Patients with Prostate Cancer, Non-Small Cell Lung Cancer and Breast Cancer Chemotherapeutic regimen was designed according to the pathological features of patients with castration-resistance prostate cancer, recurrent and refractory non-small-cell lung cancer (clinical trial no. NCT02889666) and patients with infiltrative ductal breast cancer (clinical trial no. NCT02897700). Patients with clinical staging of prostate cancer below T2a and without significant distal metastatic lesions were recruited to the clinical cohort. Patients with primary lung cancer above I subtype A (IA) (T1a, N0, M0) but without significant distal metastatic lesions were recruited to the clinical cohort. At the same time, patients over 75 years and clinically diagnosed with NSCLC, or older than 18 years of age and histologically confirmed with infiltrating BCa were recruited. All patients were provided with informed consent and signed confirmation. Data on tumor size, tissue type, tumor penetration, lymph node metastasis, and the stage of pathological TNM disease were obtained from the pathological recording system. Tumors processed as FFPE samples and processed into histological sections for evaluation. OCT frozen sections were selectively isolated by LCM for gene expression analysis. In particular, according to previously reported methods (Sun et al., 2012), gland-associated stromal cells before and after chemotherapy were isolated by LCM. The immune activity score (IRS) was classified as 0-1 (negative), 1-2 (weak), 2-3 (medium), 3-4 (strong) according to the histochemical staining of each tissue sample (Fedchenko and Reifenrath, 2014). The diagnosis of NSCLC and BCa samples was evaluated and scored by independent pathologists. The randomized control trial (RCT) protocol and all experimental procedures were approved and authorized by IRB, school of medicine, Shanghai Jiao Tong University, and progressively carried out according to authoritative guidelines.

11. Procedure of Tumor Xenografting and Preclinical Chemotherapy in Mice

All experimental mouse experiments were carried out in strict accordance with the relevant regulations of the Institutional animal care and use committee (IACUC) of the shanghai Institute of Life Sciences of the Chinese Academy of Sciences. ICR-SCID mice at an age of about 6 weeks (about 25 g in body weight) were used in this patent-related animal experiment. Stromal cells PSC27 and epithelial cells were mixed at a ratio of 1:4, with each implant containing $1.25 \times 10^6$ cells for tissue recombination. The transplant tumor was implanted into mice subcutaneously, and the animals were euthanized at the end of Week 8 after transplantation. The tumor volume was calculated according to the following formula: $V=(\pi/6) \times ((l+w)/2)^3$ (V, volume; l, length; w, width). Similarly, lung and breast cancer xenograft tumors were formed by tissue recombination with A549 (non-small cell lung cancer cell line) and W138 (lung fibroblast line), MDA-MB-231 (triple negative breast cancer cell line) and HBF1203 (breast fibroblast line), respectively.

In the preclinical chemotherapy trial, mice subcutaneously transplanted with tumors were fed standard experimental diet. After 2 weeks, the chemotherapeutics mitoxantrone (dose of 0.2 mg/kg) and/or SASP inhibitors (500 µl, dose of 10 mg/kg, RAD001, SB203580 and 5Z-7 were purchased from Tocris; LYTAK, purchased from Lilly Co ((Indianapolis, Ind.), 5 mg/kg) were administrated intraperitoneally. The timepoint was the first day of Week 3, 5, 7, and the whole course of treatment was composed of three cycles of administration, each cycle lasted for 2 weeks. After the course of treatment, mouse kidney was collected for tumor measurement and histological analysis. Each mouse received cumulatively 0.6 mg mitoxantrone/kg body weight and 30 mg SASP inhibitor/kg body (15 mg/kg body weight for LYTAK1). Mice xenografted with lung cancer and breast cancer tumor received bleomycin (totally 0.3 mg/kg) and doxorubicin (totally 0.2 mg/kg), respectively. The timepoints and frequency were same as the administration of mitoxantrone. The chemotherapeutic trial was performed until the end of Week 8, and the mice were dissected immediately after death. The transplant tumors were collected and used for analysis in a pathological system.

12. Biostatistics Methods

All in vitro experiments involving cell proliferation, migration, invasiveness and survival in this application, and in vivo tests of tumor transplantation and chemotherapy treatment in mice were repeated more than three times, and the data were presented in the form of mean±standard errors. The statistical analysis was based on the raw data and was calculated by one-way analysis of variance or a two-tailed student's t-test, while the results of $p<0.05$ were considered to have significant differences.

II. Example

Example 1. The ATM-TRAF6-TAK1 signaling axis regulates the activation of NF-κB complex in acute response to DNA injury in stromal cells, which is closely related to the expression of downstream effectors of chronic SASP.

It has been previously reported that within 48 hours of DNA damage, stromal cells exhibit a specific physiological response in the short term, presenting an acute stress-associated phenotype (ASAP). Many secreted factors throughout the whole genome are highly upregulated during formation of this phenotype, and the phenotype will then gradually transit into the senescence-associated secretory phenotype (SASP), a chronic, long-term and stable state. However, what changes have taken place in cells under the action of DNA damage, which signaling pathways play a key role, and which molecular and cellular mechanisms have been regulated in the period from ASAP (generally 1-2 days) to SASP (taking 6-8 days) remains unclear. Moreover, whether ATM, a key kinase that senses the signal of DNA damage, plays a key role in cells, has been a hot topic to many scientists worldwide in recent years.

For this purpose, the present inventor first used ChIP to analyze the stromal cell lysates after bleomycin treatment using phosphorylated ATM (p-ATM) antibody, and found that there was an interaction between activated ATM and TRAF6, which could be abolished by ATM inhibitor KU55933 (FIG. 1). Because ATM can activate TRAF6-mediated poly-ubiquitination (polyubiquitination) and lead to downstream reactions including TAK1 activation upon binding to TRAF6, the present inventor then analyzes whether there is a similar phenomenon in stromal cells. To this end, cell lysates were detected with anti-traf6 using IP after bleomycin treatment of stromal cells, we noticed rapidly growing auto-ubiquitination (monoubiquitination) of TRAF6, which confirmed its ubiquitin ligase (ubiquitin ligase) activity in damaged cells. The present inventor subsequently performed a further IP analysis using phosphorylated TAK1 (p-TAK1) antibody and found a physical interaction between TAK1 and TRAF6, which emerged immediately after DNA damage but could be abolished by TAK1 inhibitor 5z-7-oxozeaenol (henceforth abbreviated as 5Z-7) (FIG. 2). In contrast, there was no such interaction between TAK1 and ATM, though both molecules were rapidly activated after DNA damage. Meanwhile, the data also imply the specificity of the action between TAK1-TRAF6 (FIG. 2). As supporting evidence, anti-TRAF6 antibody-mediated IP experiments showed that TRAF6 could interact with both ATM and TAK1 in the activated state, suggesting that TRAF6 could act as an intermediate molecule to transmit ATM signal to TAK1 (FIG. 3). Meanwhile, knockout of TRAF6 can abolish TAK1 activation but not ATM activation in damaged stromal cells, again confirming the special role of TRAF6 in mediating ASAP acute response signaling.

Even so, is TAK1 activated indirectly by upstream DDR signaling associated with activation of a core transcription factor, NF-κB complex involved in the broad-spectrum expression of the SASP? The NF-κB complex was previously reported to be mediated by mono-ubiquitination of IκB kinase subunit γ (IKKγ) in cytoplasm. After isolating nucleus from cytoplasmic proteins using a kit, the inventor finds that TAK1 phosphorylation is associated with nuclear translocation of p50 and p65, the two main subunits of NF-κB complex (FIG. 4). However, in the presence of 5Z-7, both the phosphorylation of TAK1 and the nuclear translocation of p50/p65 were significantly inhibited, demonstrating that NF-κB activation as an event downstream of the signaling pathway mediated by TAK1 in the cytoplasm of stromal cells (FIG. 4).

Example 2. TAK1 mediates the activation of the p38MAPK signaling pathway under conditions of DNA damage, but the inhibition of its kinase activity with drugs does not affect the DNA damage response and the proliferation potential of stromal cells.

Figure 10:
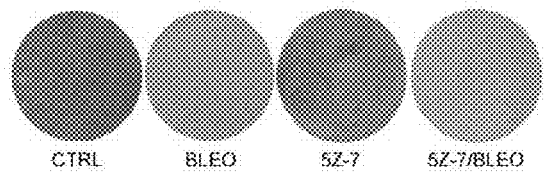
FIG. 10. Representative pictures of detection of cell clony formation. PSC27 cells were fixed on Day 7 after bleomycin and/or 5Z-7 treatment to determine colony number.
Figure 11:
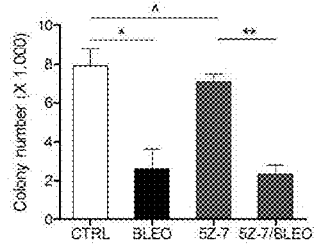
FIG. 11. Comparative analysis of colony numbers in FIG. 10.

Since the DNA damage response (DDR) signaling is delivered from nucleus to cytoplasm by phosphorylated ATM and subsequently amplified by the TRAF6/TAK1 signaling axis leading to activation of NF-κB complex, the present inventor questions whether and how these signals activate multiple molecules associated with the development of SASP. Mass data have shown that TAK1 can activate members of MAPK family such as p38, Jnk and Erk in multiple physiological processes including local inflammatory occurrence and tissue homeostasis maintenance. The present inventor proposes that TAK1 is associated with the chronic progression of SASP. First, the present inventor analyzed the change of TAK1 activity of stromal cells after treatment of bleomycin in the presence or absence of 5z-7-oxozeaenol (briefly described as 5Z-7, named as resorcylic acid lactone). The stromal cell lysate collected in vitro was detected by IP and in vitro kinase assay, and it was found that DNA damage activated TAK1, resulting in phosphorylation, which could be confirmed by the interaction between TAK1 and MKK6 (FIGS. 5-6). However, the increasing 5Z-7 makes the activation of TAK1 in damaged stromal cells gradually reduce, whereas the activation of TAK1 can be largely abolished with 500 nM 5Z-7. Meanwhile, Western blot results show that p38MAPK is also phosphorylated in damaged cells, which is parallel to TAK1 activation, suggesting a certain association between the two kinases in stromal cells in the context of gene toxicity (FIGS. 5-6). Since IL-1α is a known upstream regulatory factor for TAK1, the present inventor speculates that TAK1 can be activated under such condition by the cytokine IL-1α, which is also an effector of SASP and can further enhance the SASP phenotype once it has been upregulated and released. Thus, the inventor used IL-1α to treat PSC27 cells and found significantly enhanced TAK1/MKK6 interaction and significantly increased p38 kinase activity, which is very similar to the change of PSC27 cells treated with bleomycin (FIG. 5-6). To further verify the biological role of IL-1α during TAK1 activation, the inventor used shRNA to knock out IL-1α prior to bleomycin treatment. Interestingly, the deletion of IL-1α resulted in a significant decrease in TAK1 and p38MAPK activation in damaged stromal cells, indicating that TAK1 activation was regulated by IL-1α in cells treated with these genotoxic drugs (FIG. 7). However, it is noteworthy that TAK1 activation does not alter the DNA damage response. Once the cells were treated with bleomycin, the single-cell level of DDR foci did not change significantly in the presence or absence of 5Z-7 (FIGS. 8 and 9). Meanwhile, the colony forming ability of PSC27 cells depends on DNA damage, but is not associated with the inhibition of TAK1 activity or not (FIGS. 10 and 11).

Figure 12:
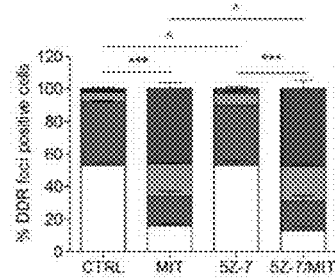
FIG. 12. Immunofluorescence staining of DNA foci in PSC27 cells after mitoxantrone and/or 5Z-7 treatment. DDR is counted and compared statistically per category.
Figure 13:
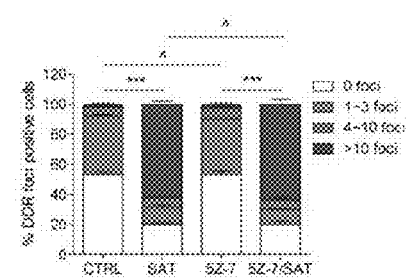
FIG. 13. Immunofluorescence staining of DNA foci in PSC27 cells after satraplatin and/or 5Z-7 treatment. DDR is counted and compared statistically per category.
Figure 14:
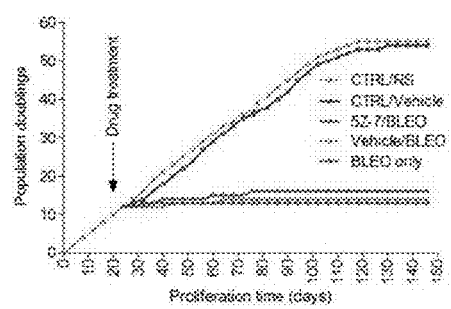
FIG. 14. Analysis of the proliferation potential of stromal cells. The PSC27 was treated with bleomycin (50 ug/ml) and/or 5Z-7 (500 nM) and then successively proliferated and subcultured under in vitro culture conditions. The proliferation fold to the culture time was plotted.

To exclude the off-target effect of bleomycin, the present inventor subsequently treated the same batch of stromal cells using two other chemotherapeutics, including mitoxantrone (a DNA topoisomerase inhibitor) and satraplatin (SAT, a platinum analogue), which can cause DNA damage through different mechanisms. As a result, the present inventor obtained DNA damage results similar to those of bleomycin treatment group (FIGS. 12 and 13). This again suggests that the DNA damage response is objectively dependent on the extent of the damage caused by the genetic drug, rather than the inhibition of TAK1 activity. Further, the inventor revealed that functional defects of TAK1 do not affect the proliferation potential of cells in vitro, which can be confirmed by the doubling curve of cell population, an assay specifically used to evaluate the maximal proliferation capacity displayed by cells during continuous passage under culture conditions (FIG. 14).

Figure 15:
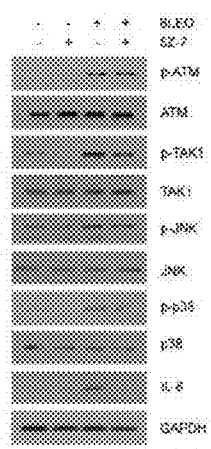
FIG. 15. The stromal cells were collected on Day 7 after bleomycin and/or 5Z-7 treatment. The lysates were analyzed by Western blot for their phosphorylation levels of ATM and TAK1, and activation of TAK1 downstream substrate JNK and p38. IL-8, a chemokine was used as a marker secreted factor of SASP, whose expression level was simultaneously analyzed.

In addition, the present inventor examined whether the phosphorylation state of ATM is altered when TAK1 activity is inhibited after the cells were subjected to genotoxic damage, that is, whether the inhibition of TAK1 affects the DNA damage reaction intensity from another perspective. Western blot data suggest that the phosphorylation status of ATM stimulated by DNA damage does not depend on whether TAK1 activity is inhibited by 5Z-7, though the phosphorylation of JNK and p38MAPK decreased significantly when TAK1 was inhibited (FIG. 15). Furthermore, the protein expression level of a typical marker for development of the SASP phenotype, IL-8 were significantly downregulated when DNA damage persisted. In summary, the experimental data consistency of the present inventor indicates that the maintenance of TAK1 activity is essential for the chronic development of SASP.

Example 3. The mTOR pathway downstream of TAK1 plays an important role in the development of the chronic phase of the SASP.

Figure 16:
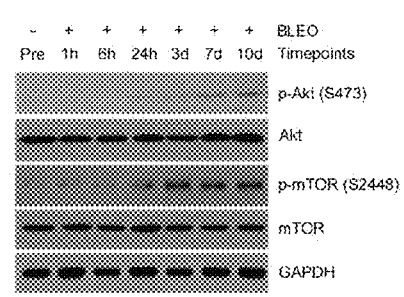
FIG. 16. After bleomycin treatment of stromal cells, the phosphorylation levels of AKT and mTOR were collected at different timepoints and analyzed by Western blot.
Figure 17:
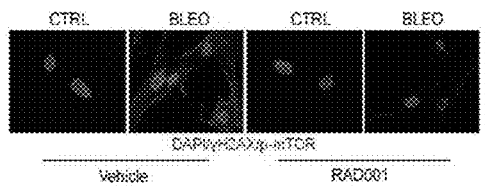
FIG. 17. p-mTOR expression level of PSC27 cells on Day 7 after bleomycin (50 ug/ml) and/or RAD001 (50 nM) treatment by immunofluorescence assay.
Figure 18:
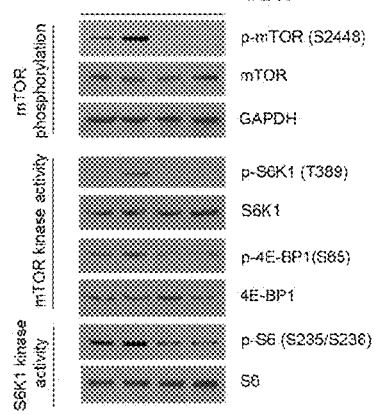
FIG. 18. The activation of its mTOR and its downstream substrate S6K1/4E-BP1 on Day 7 after treatment of stromal cells with bleomycin and/or RAD001 by Western blot.
Figure 19:
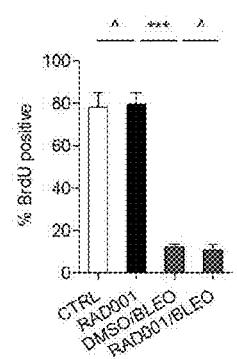
FIG. 19. After the stromal cells were treated with bleomycin and/or RAD001, cells were collected and detected for BrdU incorporation in DNA on Day 7.

DNA damage promotes the formation of senescent cells, which remain both metabolically and physiologically active for several months, while exhibiting significantly increased lysosomal mass and enhanced SA-B-Gal activity. Since TAK1 and other molecules have a key signaling role in the ASAP acute phase after DNA damage, the inventor questioned if any other molecules are also activated during the acute cellular response and promote the chronic development of SASP. The inventor's data show that Akt/mTOR activation begins in the late phase of the acute response after DNA damage, which can be confirmed by posttranslational modification of the two sites, Akt (ser473) and mTOR (ser2448), both of which begin to be phosphorylated 24 hours after bleomycin treatment and enter the platform period after 7 days (FIG. 16). Immunofluorescence assay showed that activated mTOR appeared in cytoplasm. The inventor subsequently detected changes in the pathways and key molecules upstream and downstream of mTOR. For example, phosphorylation of two substrates downstream of mTOR, S6K1 and its catalytic subunits, S6 and 4E-BP1, simultaneously indicated the functional activation of mTOR (FIG. 17). The inventor has recently reported that rapamycin can reduce the phosphorylation of S6K1 and 4E-BP1 in senescent fibroblasts caused by radiation conditions, and can negatively regulate the translation of mRNA with stable secondary structure by intracellular helicase machine. In the present inventor, RAD001, a rapamycin analogue, was used and found to similarly cause inhibition of S6K1 and 4E-BP1 activation when mTOR phosphorylation is blocked, confirming the efficacy of rapamycin as a SASP inhibitor (FIG. 18). Nevertheless, bleomycin-induced DDR foci remained unchanged in damaged stromal cells (FIG. 17), while cell cycle arrest and SA-β-Gal activity remained unaffected in the presence of RAD001, suggesting that both cellular senescence and metabolic activity were maintained (FIGS. 19 and 20).

As the cellular senescence-related transcriptome is regulated by several major transcription machines, including NF-κB, the present inventor asked whether mTOR is directly or indirectly related to activation of the NF-κB complex. To this end, the present inventor analyzed the stromal cells treated with bleomycin and found the degradation of IκBα and the stabilization of the subunit p65 (ReIA) of NF-κB in its cytoplasm, both indicated the activation state of NF-κB complex in DNA-damaged cells (FIG. 21). Meanwhile, data from the reporter vector transfection experiment also confirmed a significant upregulation of NF-κB transcriptional activity, but could be significantly attenuated in the presence of RAD001 (FIG. 22). The present inventor subsequently performed IP experiments using mTOR antibodies and found an interaction between IKKα and Raptor (FIG. 23), whereas a data from a reverse IP mediated by IKKα antibody showed the association between IKKα and mTOR, but not Raptor (FIG. 23). Therefore, a series of experimental results suggest that IKKα may play a different role in IKK complex from other subunits because of the special potential of its physical interaction with mTOR to activate NF-κB complex.

To further verify the interrelationship between mTOR and IKK complex, the present inventor uses PP242, a second generation small molecule inhibitor of mTOR that targets mTOR kinase activity by competitively binding ATP sites, i.e., in a manner distinct from that of rapamycin and its analogues. In vitro kinase assay showed that IKKα in stromal cells after DNA damage was phosphorylated as a downstream substrate of mTOR (FIGS. 24 and 25). Despite the direct interaction between mTOR and IKKα, the role of IKKβ, another catalytic subunit of IKK complex in this process, remains unknown. To clarify this, the present inventor used shRNA to knock out the above two subunits separately and transfected the NF-κB activity reporter vector into cells prior to drug treatment. Interestingly, the clearance of IKKα significantly reduced the nuclear activity of NF-κB, but the deletion of IKKβ resulted in a greater signal decline. When both subunits were knocked out, only the lowest intensity of NF-κB activity remained in the nucleus (FIG. 26). These data indicated that IKKα and IKKβ are activated in stromal cells after DNA damage.

Figure 27:
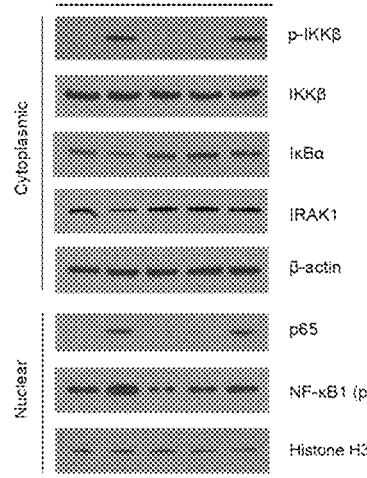
FIG. 27. The stromal cells were treated with bleomycin and/or RAD001, and stimulated with IL-1α (20 ng/ml), its phosphorylation of IKKβ, IkBα and IRAK1 protein expression, and p65/p50 nucleation were analyzed by Western blot. β-actin and Histone H3 were loading controls for cytoplasmic and nuclear samples, respectively.
Figure 28:
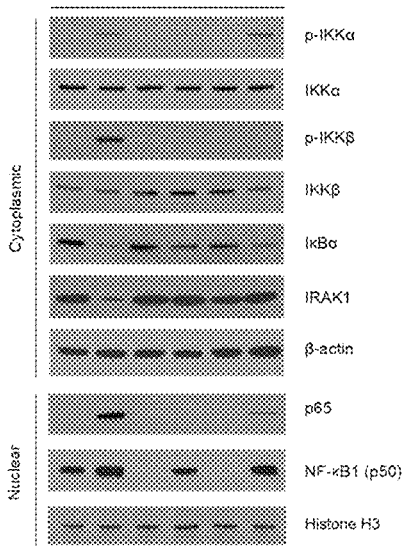
FIG. 28. After shRNA-mediated knockout of IL-1α, stromal cells were treated with bleomycin and/or RAD001, and then analyzed by Western blot for their phosphorylation of IKKα and IKKβ, IkBα and IRAK1 protein expression, and p65/p50 nuclear translocation. β-actin and Histone H3, protein loading controls.

The inventor recently found that mTOR can regulate the expression of the broad-spectrum effectors of SASP by restricting the translation of the cytokine IL-1α, during which NF-κB complex is inhibited. However, how IL-1α controls NF-κB transcription activity and which IKK subunit specifically mediates the signaling pathway of IL-1α excitation is unclear. Here, the inventor discovered that phosphorylation of IKKβ, degradation of IRAK1 and IkBα, and nuclear translocation of subunits p65 and p50 of NF-κB complex all occur after DNA damage (FIG. 27). Although these changes were largely abolished after RAD001 was added to the medium, the addition of IL-1α was able to reverse them. On the other hand, knockout of IL-1α was able to reduce the level of IKKβ activation, whereas IKKα activity remained unchanged (FIG. 28). Although the IRAK1 protein level was largely unchanged, the total amount of IkBα protein appeared significantly reduced, suggesting that IKKα mediates NF-κB signaling in this process. In addition, signaling of p65 and p50 in the nucleus remains largely maintained, even in the case of knockout of IL-1α, indicating the persistently activated NF-κB complex (FIG. 28).

Figure 29:
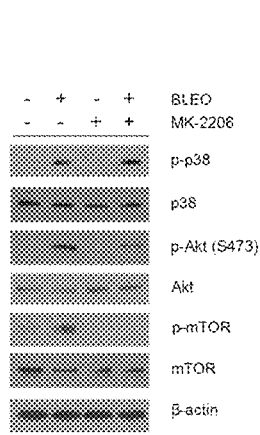
FIG. 29. The stromal cells treated with the Akt inhibitor MK2206 were collected and lysed 7 days after bleomycin injury, and the activation of p38, Akt and mTOR was analyzed by Western blot.
Figure 30:
FIG. 30. The catalytic subunit p110 of PI3K was knocked out by shRNA and the stromal cells were then treated by bleomycin. On Day 7 after injury, the cells were lysed and analyzed for their p38, Akt, mTOR activation, and changes in p110 and p85α expression levels.
Figure 31:
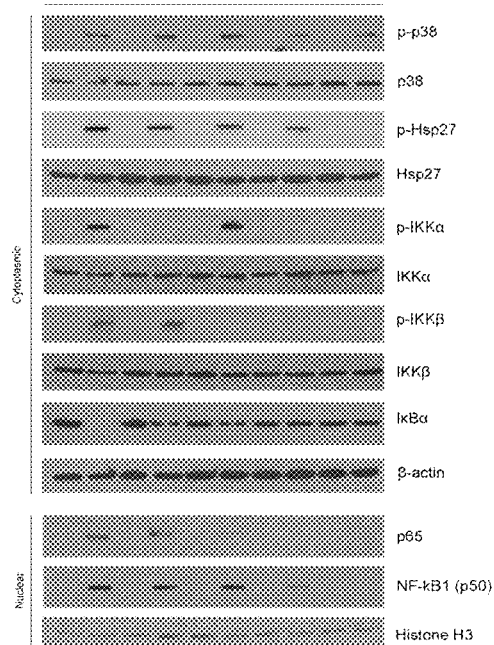
FIG. 31. After IKKα and IKKβ were knocked out by shRNA, respectively, the stromal cells were treated with bleomycin and/or Sb203580 and collected and lysed on Day 7. The activation levels of p38 and its substrates HSP27, IKKα and IKKβ, and the nuclear translocation of subunits of NF-kB were analyzed by Western blot.
Figure 32:
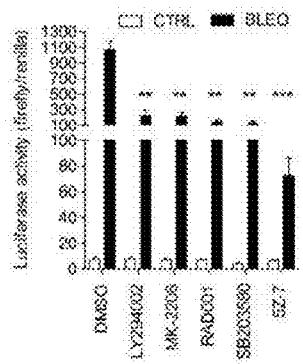
FIG. 32. Detection of NF-kB transcriptional activity based on the reporter vector. Stromal cells were treated with bleomycin along with the PI3K small molecule inhibitor LY294002 (1 μM), Akt inhibitor MK-2206 (100 nM), mTOR inhibitor RAD001 (50 nM), p38 inhibitor SB203580 (10 μM) and TAK1 inhibitor 5Z-7 (500 nM), respectively, and cell lysates were used for determining luciferase activity.
Figure 33:
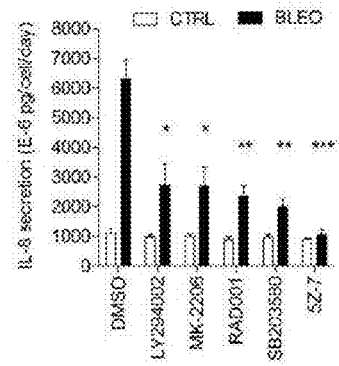
FIG. 33. The extracellular fluid released by each group of cells were tested by ELISA to determine the protein expression level of the secreted factor IL-8.

Next, the present inventor analyzed whether this classical signaling pathway of PI3K/Akt is associated with mTOR activation in stromal cells in the context of DNA damage. The activity of mTOR was significantly downregulated in stromal cells upon simultaneous treatment of bleomycin and MK-2206 (a small molecule inhibitor of Akt) (FIG. 29). In addition, PI3K catalyzed the downregulation of subunit p110, largely preventing the activation of Akt and mTOR in damaged PSC27 cells (FIG. 30). In contrast, p38 remained always activated in bleomycin-treated stromal cells, regardless of the integrity of the PI3K/AKT pathway (FIG. 30), suggesting that p38 acts as a factor upstream of PI3K/AKT/mTOR in these stromal cells. Further results showed that deletion of either IKKα or IKKβ failed to reduce the activity of p38, though the p38 inhibitor SB203580 could significantly reduce the phosphorylation level of this kinase (FIG. 31). The expression of NF-κB activation and chemokine IL-8 protein levels induced by DNA damage was significantly reduced when the small molecule inhibitors LY294002, MK-2206, SB203580, or 5Z-7(targeting PI3K, Akt, p38 or TAK1, respectively) were added to the medium, though 5Z-7 appeared to have a stronger inhibitory effect (FIGS. 32 and 33). Since 5Z-7 primarily targets the kinase TAK1, the above data demonstrate that SASP can be specifically controlled by a kinase from signaling nodes more upstream of the network, eventually achieving higher inhibition efficiency as a whole.

Example 4. TAK1 inhibition can reverse multiple malignant phenotypes of cancer cells conferred by damaged stromal cells in vitro.

Figure 34:
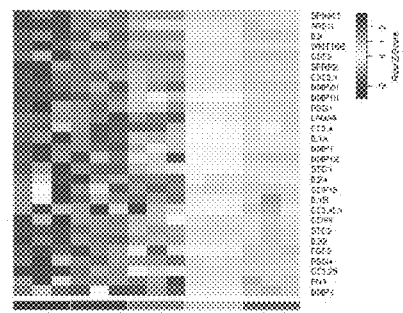
FIG. 34. After simultaneous treatment of PSC27 cells with bleomycin and/or 5Z-7, SB203580 (SB) and RAD001, total RNA was analyzed by microarray for expression-spectrum. The heatmap showed the expression-spectrum difference between several groups of samples.

Experimental data of the present inventor confirm that the formation of SASP can be effectively interfered from its upstream signaling pathway, then can the control of TAK1 activity have a certain biological effect, especially a series of phenotypes of cancer cells enhanced by damaging stromal cells in the microenvironment? First, the present inventor examines which genes are significantly downregulated when SASP is inhibited. Comparative transcriptomic data showed that in the case of treatment with bleomycin alone and in combination with 5Z-7, the latter could cause most of the SASP effectors to be significantly inhibited (FIG. 34). The 5Z-7-mediated inhibition of TAK1 activity seems to be more effective in downregulating most secreted proteins of SASP than bleomycin/SB20580 and bleomycin/RAD001 combination treatments. Although there are some variations between the decline extent of different SASP factors, the general consensus trend suggests that the broad-spectrum SASP is largely controlled.

Figure 35:
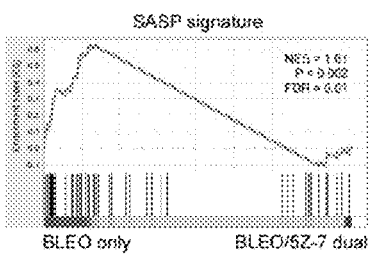
FIG. 35. GSEA evaluation of relative expression of SASP-specific expression signature in stromal cells treated with bleomycin and/or 5Z-7. NES, normalized enrichment score; FDR, false discovery rate.
Figure 36:
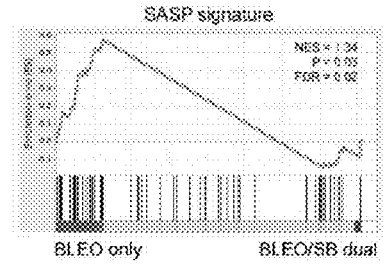
FIG. 36. Similar to FIG. 35, GSEA analysis of the expression differences caused by the SASP signature between bleomycin and/or SB203580.
Figure 37:
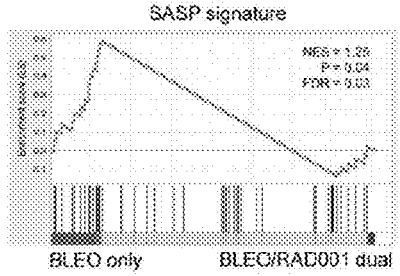
FIG. 37. Similar to FIG. 35, GSEA analysis of the expression differences caused by the SASP expression signature between bleomycin and/or RAD001.
Figure 38:
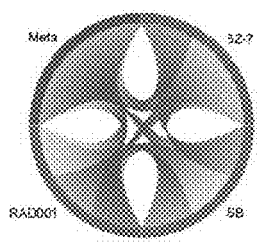
FIG. 38. String diagram showed the interrelationship between factors significantly downregulated by 5Z-7, SB or RAD001, respectively (fold change>2) in stromal cells. Meta, a set of meta databases formed from combining data generated by the three inhibitors, respectively to enhance statistical power and inter-group effectiveness.
Figure 39:
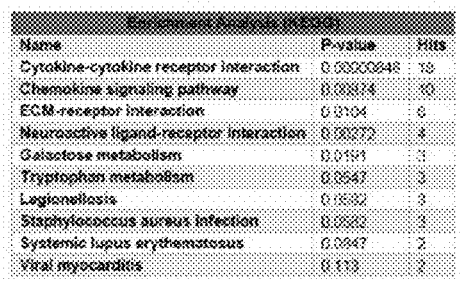
FIG. 39. KEGG pathway analysis and evaluation of biological relationships between the top 809 genes specifically downregulated by 5Z-7 (fold change>2). An IMEx interactome database was used for protein-protein interaction analysis.
Figure 40:
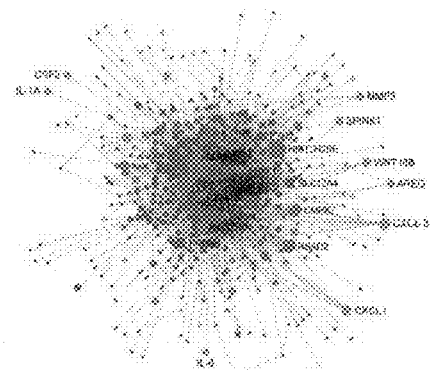
FIG. 40. Signaling node network constructed by the top 809 genes in FIG. 39. Green, canonical SASP factor. Line, putative protein-protein interactions.
Figure 41:
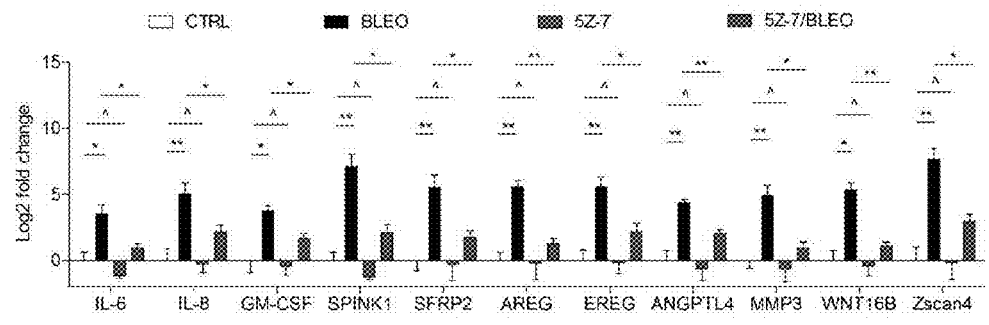
FIG. 41. Fluorescence quantitative RT-PCR analysis of expression changes of multiple SASP factors in stromal cells following bleomycin and/or 5Z-7 treatment.

Under the premise that TAK1 activity inhibition can cause the overall expression of SASP to be attenuated, the inventor evaluates the development of SASP using Gene Set Enrichment Analysis (GSEA). According to a SASP-specific expression signature previously defined by secreted factors closely related to the human stromal cell SASP published by the present inventor in recent years, there was a significant downregulation of the signature when TAK1 was inhibited by drugs (FIG. 35). Although the expression signature of SASP is also significantly weakened when p38 or mTOR is inhibited, the control effect in both cases is not as good as the data when TAK1 activity is inhibited (FIGS. 36 and 37). In addition, the present inventor further extended the results. With data derived from the meta-analysis-based human protein interaction network analysis, the inventor showed a systematic association of the downregulated interactions between multiple proteins with cytokine/chemokine/extracellular matrix receptor upon TAK1 inhibition, and signaling pathway crosstalk (FIGS. 38, 39 and 40). The above results further verified the biological effects of TAK1 inhibition (FIG. 41).

Figure 42:
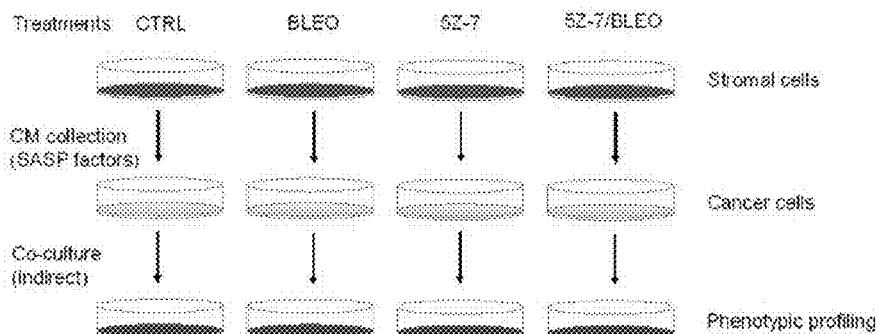
FIG. 42. Experimental flow chart of stromal cell culture, drug treatment, indirect co-culture with cancer cells and phenotypic measurement under in vitro conditions.
Figure 43:
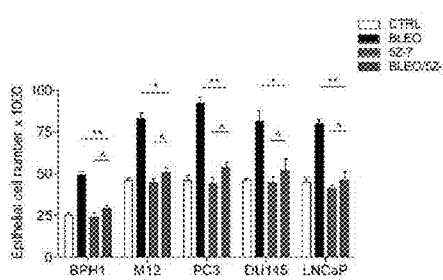
FIG. 43. The tendency of stromal cell extracellular fluid to promote the proliferation of prostate cancer epithelial cells decreased significantly under the action of 5Z-7.
Figure 44:
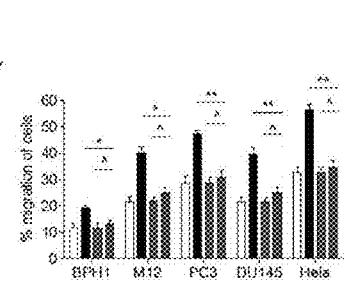
FIG. 44. The ability of stromal cell extracellular fluid to promote the in vitro migration of prostate cancer epithelial cells was significantly reduced under the action of 5Z-7.
Figure 45:
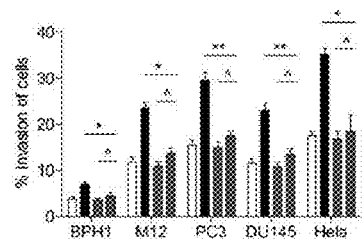
FIG. 45. The capacity of stromal cell extracellular fluid in promoting the invasion of prostate cancer epithelial cells was significantly weakened under the action of 5Z-7.
Figure 46:
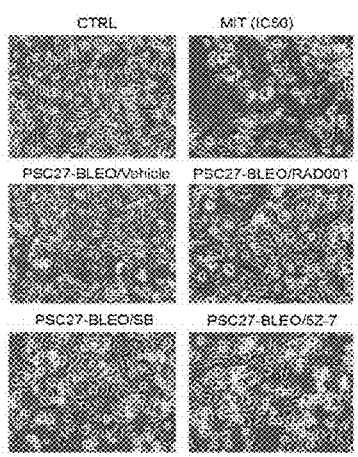
FIG. 46. Morphological changes of prostate cancer PC3 cell lines upon drug treatment in vitro. Results of the treatment with SASP inhibitors RAD001, SB203580 and 5Z-7 simultaneously along with MIT, or those of MIT treatment alone were compared in parallel.
Figure 47:
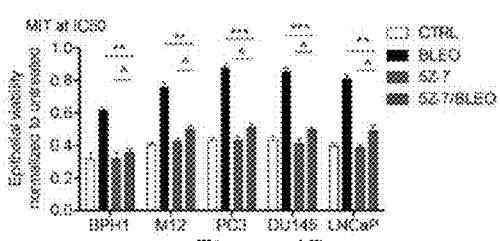
FIG. 47. After several different ways of drug treatment, the extracellular fluid of PSC27 cells were collected, which was subsequently used to culture prostate cancer epithelial cell lines (BPH1, M12, PC3, DU145 and LNCaP), while the statistical comparison of the number of cells that survived after addition of mitoxantrone at IC50 concentration was performed.
Figure 48:
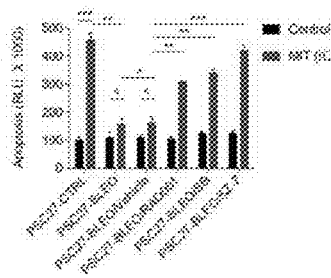
FIG. 48. Comparison of apoptosis indices of PC3 cells cultured under different conditions in the extracellular fluid collected from PSC27 treated with mitoxantrone (IC50 concentration) and several SASP inhibitors (including 5Z-7). Results of detection of caspase 3/7 activity were directly used for plotting.
Figure 49:
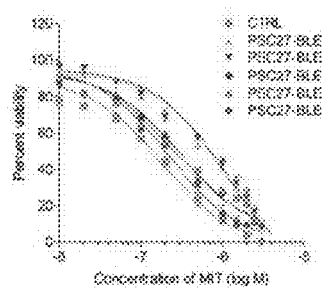
FIG. 49. The cell survival rate of PC3 cells treated with the extracellular fluid produced by each subline of PSC27 in the presence of different concentrations of mitoxantrone compared to of that the untreated control group. Dose response curve, nonlinear regression.

Subsequently, the inventor evaluated the effect of TAK1 inhibition of stromal cells on the proliferation of cancer cells. The inventor collects their extracellular fluid and immediately used in the culture of prostate cancer cells on Day 7 after PSC27 was treated with bleomycin (FIG. 42). Interestingly, the proliferation rate of epithelial cancer cells was reduced significantly when TAK1 was inhibited (FIG. 43). Although the extracellular fluid of the damaged stromal cells can significantly improve the migration and invasion rate of cancer cells, these changes were significantly reduced when stromal cell TAK1 was inhibited (FIGS. 44 and 45). More importantly, resistance of cancer cells to mitoxantrone conferred by the extracellular fluid of stromal cells when SASP occurred was significantly weakened, suggesting that intracellular TAK1 activity control induced by 5Z-7 could counteract the acquired survival of cancer cells when the stromal cells were damaged (FIG. 45 and FIG. 46). Accompanied by a decline in cancer cell survival was the rise in apoptosis index exhibited by cells when mitoxantrone was used to treat cancer cells, a change that can be confirmed by caspase 3/7 activity assay (FIG. 47). The dramatic change in the drug resistance potential of cancer cells was further confirmed by the cell survival non-linear curve caused by mitoxantrone in the concentration range of 0.1-1 µM, which basically coincided with serum levels in patients with prostate cancer in clinics (FIG. 48). Therefore, in either case, data of the reduced acquired malignancy of cancer cells caused by the inhibition of stromal cell TAK1 activity was more significant than the results induced by RAD001 and SB203580 (FIG. 49).

Figure 50:
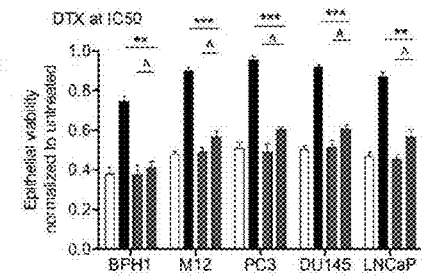
FIG. 50. The parallel comparison of cell number when the extracellular fluid of stromal cells was used to treat prostate cancer epithelial cell lines, which was simultaneously treated with microtubule-toxic drug docetaxel (DTX) (IC50 concentration).
Figure 51:
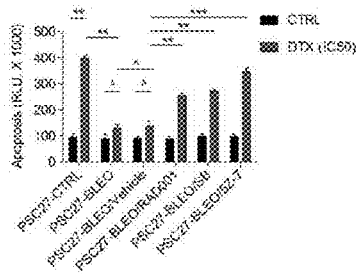
FIG. 51. Comparison of apoptosis index of PC3 cell under the treatment of several drug combinations. Caspase 3/7 activity values were used for apoptosis test.
Figure 52:
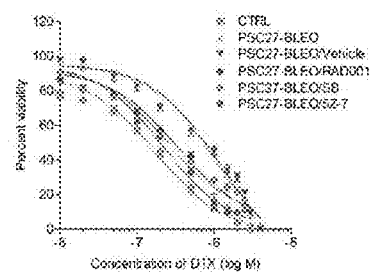
FIG. 52. Comparison of cell survival rate under treatment of several different drug combinations. Dose response curve, nonlinear regression.

To further extend above findings, the inventor used the same set of conditioned media to treat cancer cells exposed to docetaxel. It was found that the extracellular fluid produced by stromal cells at the time of TAK1 inhibition could improve the cytotoxicity of docetaxel to cancer cells, resulting in a decrease in cell survival, an increase in apoptosis index and a shift in the response curve of cancer cells (FIGS. 50, 51 and 52). Thus, inhibition of TAK1 activity of stromal cells by 5Z-7 can attenuate the acquired resistance of cancer cells to multiple chemotherapeutics conferred by stromal cells.

Figure 53:
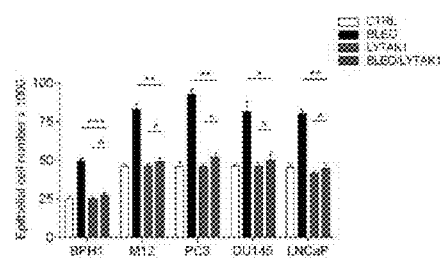
FIG. 53. The tendency of stromal cell extracellular fluid to promote the proliferation of prostate cancer epithelial cells decreased significantly under the action of another TAK1 inhibitor, LYTAK1.
Figure 54:
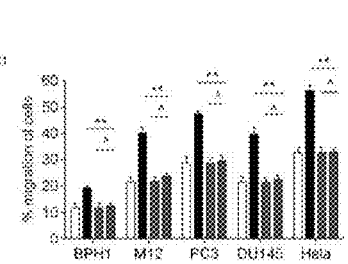
FIG. 54. The capacity of stromal cell extracellular fluid in promoting in vitro migration of prostate cancer epithelial cells was significantly reduced under the action of LYTAK1.
Figure 55:
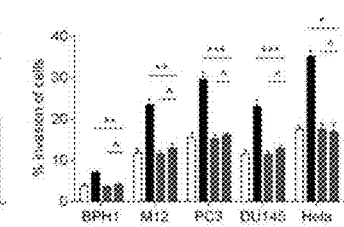
FIG. 55. The pattern of stromal cell extracellular fluid in promoting the invasion of prostate cancer epithelial cells was significantly weakened by LYTAK1.
Figure 56:
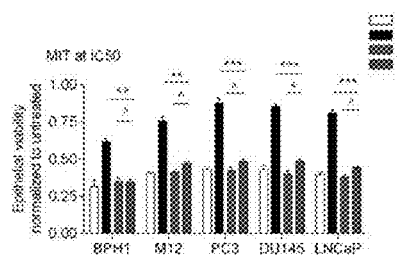
FIG. 56. The extracellular fluid were collected after exposure of PSC27 cells to several different drug treatments, and subsequently used to culture prostate cancer epithelial cell lines (BPH1, M12, PC3, DU145 and LNCaP). At the same time, the number of surviving cells was compared after adding mitoxantrone treatment to the culture at IC50 concentration.
Figure 57:
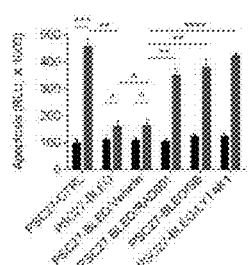
FIG. 57. The extracellular fluid were collected after treatment of PSC27 with several SASP inhibitors (including LYTAK) and used to treat PC3 cells together with mitoxantrone. Comparison of apoptosis indices under different conditions was conducted. Caspase 3/7 activity measurement results were directly used for plotting.
Figure 58:
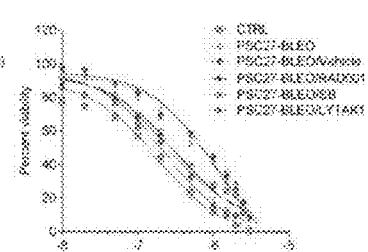
FIG. 58. The survival rate of PC3 cells treated with extracellular fluid produced by each subline of PSC27 in the presence of different concentrations of mitoxantrone compared to that of the untreated control group. Dose response curve, nonlinear regression.
Figure 59:
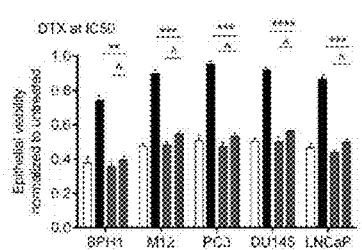
FIG. 59. Parallel comparison of cell number of prostate cancer epithelial cell lines treated with stromal cell extracellular fluid (including the LYTAK1 treatment group) simultaneously with microtubule-toxic drug docetaxel (DTX) (IC50 concentration).
Figure 60:
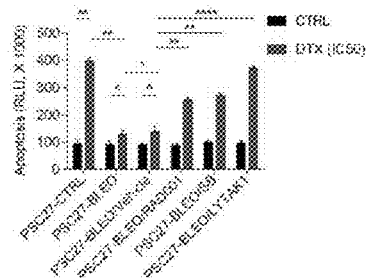
FIG. 60. Comparison of cell apoptosis indices of PC3 treated with docetaxel and several extracellular fluids of PSC27. Caspase 3/7 activity values were used for apoptosis measurement.

Meanwhile, the inventor employed another small molecule inhibitor LYTAK1 of TAK1 for in vitro experiments. The results showed that the inhibition of TAK1 mediated by LYTAK1 significantly reduced proliferation, migration and invasion of cancer cells under the action of the extracellular fluid from stromal cells (FIGS. 53, 54 and 55). Upon assessment of the resistance of cancer cells to mitoxantrone in vitro, it was found that the extracellular fluid from bleomycin-damaged stromal cells in the presence of LYTAK1 significantly reduced the resistance of cancer cells, i.e., the inhibition of intracellular TAK1 activity caused by LYTAK1 could counteract the acquired survival of cancer cells when the stromal cells were damaged (FIGS. 56, 57 and 58). In addition to mitoxantrone, a similar role was found in cytotoxic experiments with another chemotherapeutic drug docetaxel, that is, LYTAK1 significantly reduced the resistance or anti-apoptotic ability of cancer cells acquired under the action of the extracellular fluid from stromal cells (FIGS. 59, 60 and 61).

Example 5. Targeting TAK1 can effectively restore tumor sensitivity to chemotherapeutic agents by interfering with development of SASP of stromal cells in the microenvironment.

Broad-spectrum expression of SASP in the microenvironment can accelerate many malignant events, including tumorigenesis, local inflammation, and therapeutic resistance. However, whether this downward trend towards malignancy can be avoided by specifically controlling the formation of SASP in the microenvironment, and how to effectively inhibit SASP in the microenvironment activated by anticancer therapies, has always been a scientific challenge. It should be noted that TAK1 activation, which is closely related to the occurrence and development of SASP, is common in patients with prostate cancer after clinical chemotherapy (the phosphorylation level increased significantly compared with the pre-treatment period) (FIG. 62). More importantly, the activation status of TAK1 in the tumor microenvironment was significantly negatively correlated with survival of patients with prostate cancer after treatment (FIG. 63).

Figure 65:
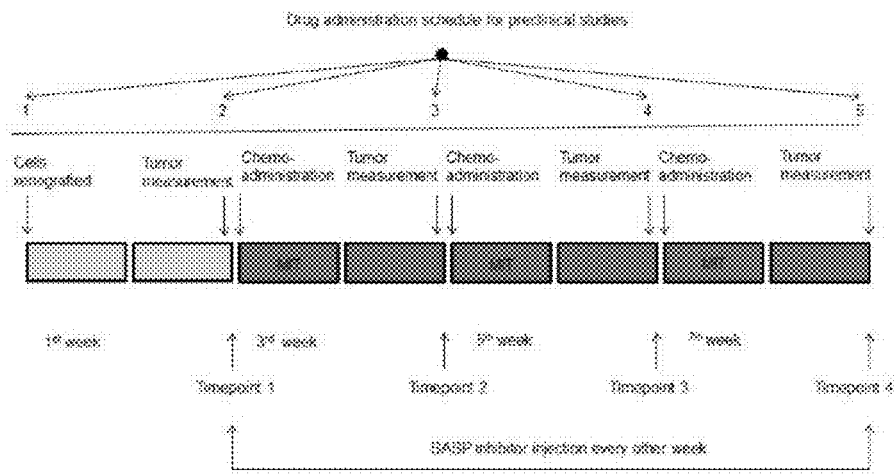
FIG. 65. Preclinical chemotherapy trial protocol. The whole process lasted for 8 weeks, and mice began to undergo drug treatment in Week 3 after tissue recombination. MIT is administered intraperitoneally every other week, 5Z-7 or LYTAK1 was administered simultaneously. When the trial finished at the end of Week 8, tumor volumes of mice were measured and histologically analyzed.
Figure 66:
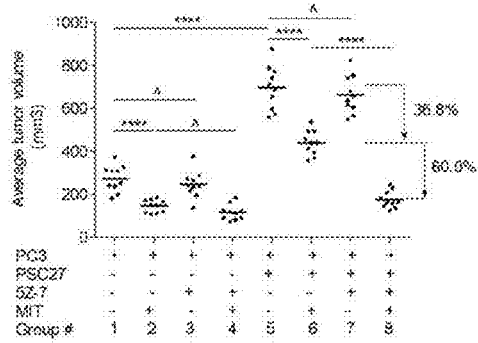
FIG. 66. Statistical comparative analysis of terminal tumor volume of mice. Compared with group 5, the volume of group 6 decreased by 37%; compared with group 6, the volume of group 8 decreased by 60%.
Figure 67:
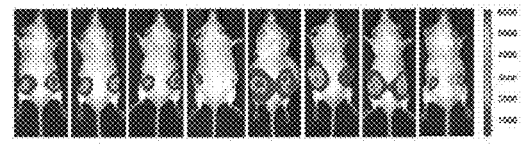
FIG. 67. Examination of tumor growth and development in vivo in each group of animals in FIG. 66 with BLI in the course of chemotherapy. The fluorescein signal indicated that the cancer cells were concentrated near hind legs subcutaneously with no signs of distal metastasis.

In order to simulate clinical conditions as much as possible, the present inventor inoculated the subcutaneous site of immunodeficient mice with an admixture of prostate-derived stromal cell line PSC27 and epithelial cancer cell line PC3. The mice subsequently underwent a regimen of 8-week preclinical chemotherapy, which included three single- or double-drug treatments based on a series of pre-experimental data (FIGS. 64 and 65). In the absence of stromal cells, PC3 cells were still able to form tumors under screening pressure caused by chemotherapeutics, though their volumes were smaller than that generated in the case of concurrent inoculation of stromal cells and cancer cells. Such difference also objectively confirmed the tumor-promoting effect of the microenvironment (FIG. 66). Although 5Z-7 itself does not appear to alter tumor growth trends, mitoxantrone administration can cause a 37% decrease in the terminal tumor volume (FIG. 65, group 5-6). Notably, the combination of MIT and 5Z-7 resulted in a further shrinkage of tumor volume by 60% (FIG. 66, group 6-8). Meanwhile, in order to ensure that the subcutaneously inoculated tumors do not develop a distal metastasis throughout the course of chemotherapy, which will make the experimental data difficult to interpret, the present inventor also inoculated a batch of PC3 and PSC27 cells integrated with luciferase reporter gene vector fragments, which enables tumor growth to be monitored in real time by bioluminescence imaging (BLI). The present inventor found that the signal intensity generated by these tumors roughly corresponds to the detected terminal tumor volumes, thus confirming the differences between groups from an alternative perspective (FIG. 67).

Figure 68:
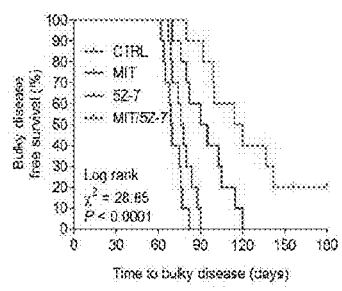
FIG. 68. Comparison of median survival curves in mice treated with several drugs or drug combinations. Significant difference is present between MIT and MIT/5Z-7, p<0.0001.

Although there was no ectopic metastasis of cancer cells, the current inventor questions whether the microenvironment causes other pathological consequences other than tumor growth and drug resistance. To this end, the present inventor evaluated the survival of multiple groups of animals under a batch of time-extended preclinical treatment conditions to determine the objective results of tumor progression. All animals were monitored for tumor volume and recognized as severe disease when the tumor volume reached a certain upper limit (size 2000 mm$^3$). In this way, the inventor found that mice in the group of mitoxantrone (MIT)/5Z-7 combination treatment obtained significantly prolonged median survival, with a prolonged disease-free survival by about 50% compared with those in the group of mitoxantrone alone (FIG. 68, comparison of the green and blue groups). However, using 5Z-7 alone only slightly prolonged the survival of mice (FIG. 68, comparison of the purple and red groups). The above results suggested that the combined use of MIT/TAK1 is ideal.

Figure 69:
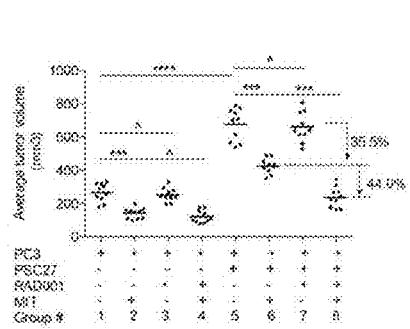
FIG. 69. Similar with FIG. 66, but mice underwent treatment of SASP inhibitor RAD001 in combination with MIT. Corresponding tumor volumes decreased by 36% and 44%, respectively.
Figure 70:
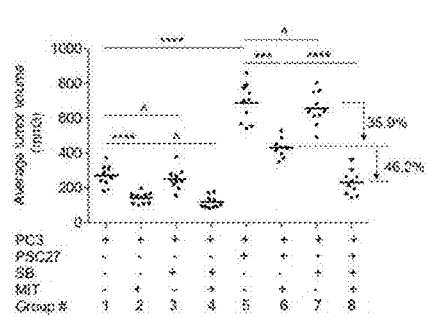
FIG. 70. Similar with FIG. 66, but mice underwent treatment of SASP inhibitor SB with MIT. Corresponding tumor volumes decreased by 36% and 46%, respectively.

The present inventor then systematically compared the difference between the effect of TAK1 inhibition and the result from reduced mTOR or p38 activity under the condition of SASP occurrence and development in the microenvironment. By conducting two groups of in vivo experiments similar to 5Z-7 administration, the inventor finds that the combined administration of MIT/RAD001 and MIT/SB203580 can significantly reduce the terminal volumes of the subcutaneous tumors at the end of the chemotherapy course. MIT/RAD001 combined medication resulted in a further decrease of 44% compared to single MIT drug delivery, while MIT/SB203580 further decreased by 46% (FIGS. 69 and 70). Although both mTOR and p38-targeted combination therapy significantly delayed tumor growth, TAK1 suppression was more effective in tumor suppression in general. To further confirm that the SASP expression of the in vivo microenvironment during the treatment was effectively controlled by the inhibitor, the present inventor used the laser capture microdissection to dissect and specifically isolate the stromal cells in the tumor and performed a transcript level analysis. Several typical SASP effectors including IL-8, AREG, SPINK1 and MMP3 were found to be significantly reduced (FIGS. 71, 72, 73, 74).

In addition, in order to further verify the effect of TAK1 targeting inhibitors and chemotherapeutic agents on tumors, the applicant used LYTAK1 in a similar preclinical experiment. It was found that the combined administration of LYTAK1 and mitoxantrone could again reduce tumor volume by 63% on the basis of mitoxantrone alone (FIG. 75). Expression of several typical SASP effectors was also generally significantly reduced under the inhibition of LYTAK1 (FIGS. 76, 77, 78 and 79).

Figure 81:
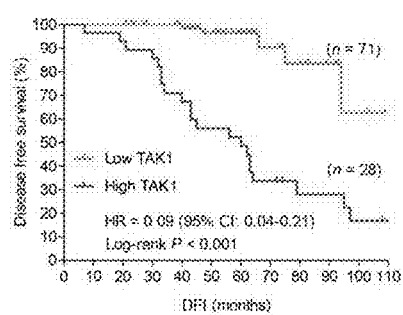
FIG. 81. Statistical analysis of NSCLC patient survival based on TAK1 activation. The number of patients with low expression of p-TAK1 was 71 and that of the high expression group was 28.
Figure 82:
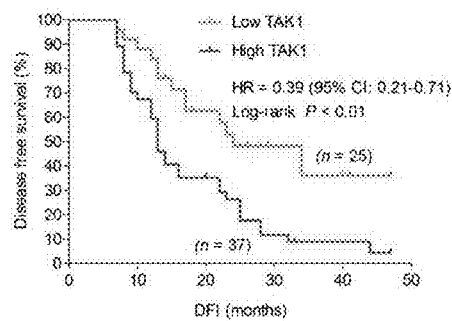
FIG. 82. Statistical analysis of BCa patients survival based on TAK1 activation. The number of patients with low expression of p-TAK1 was 25 and that of the high expression group was 37.
Figure 83:
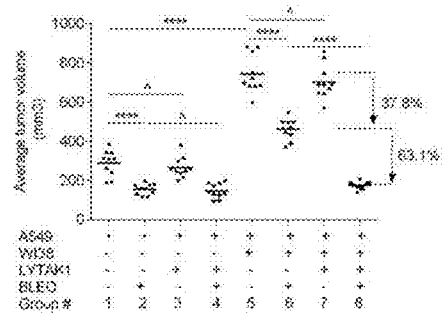
FIG. 83. Statistical comparative analysis of terminal tumor volumes in NSCLC tumors transplanted mice (NSCLC cell line A549/stromal cell line W138; LYTAK1 for administration alone or in combination with bleomycin-based chemotherapy). Compared with group 5, the volume of group 6 decreased by 38%; compared with group 6, the volume of group 8 decreased by 63%.
Figure 84:
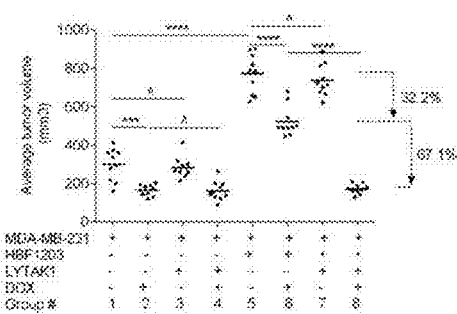
FIG. 84. Statistical comparative analysis of terminal tumor volumes in BCa tumors transplanted mice (BCa cell line MDA-MB-231/stromal cell line HBF1203; LYTAK1 for administration alone or combined with bleomycin for chemotherapy). Compared with group 5, the volume of group 6 decreased by 32%; compared with group 6, the volume of group 8 decreased by 67%.

In addition to animal experimental data that support TAK1 as an effective target for controlling the SASP phenotype in the microenvironment, the present inventor further systematically analyzed the pathological association between TAK1 and the survival of clinical patients. Results from clinical data suggest that there is a general significant negative relationship between TAK1 activity and survival of non-small cell lung cancer (NSCLC) and breast cancer (BCA) patients (FIGS. 80, 81 and 82). To demonstrate the association between TAK1 expression and the two cancer types in vivo, the inventor further performed preclinical experiments using tissue recombination-based xenograft tumor mice. Mouse treatment data showed that LYTAK1, co-administered with bleomycin and doxorubicin, could significantly reduce the terminal volume of tumors (63% for NSCLC and 67% for BCA) (FIGS. 83 and 84). Therefore, the inventor concludes that simultaneous clearance of malignantly growing cancer cell populations and control of passively activated microenvironment-associated SASP by drug by targeting TAK1, can significantly reduce tumor growth tendency, and TAK1 can be an effective new drug target for blocking the occurrence and development of microenvironment SASP in future clinical treatment.

All references referred in the invention are cited as references in this application, just as each document is individually cited as a reference. Furthermore, it should be understood that, after reading the above-mentioned contents of the invention, those skilled in the art may make various changes or modifications to the invention, and these equivalent forms also fall within the limits of the claim annexed to the application.

The invention claimed is:

1. A method for inhibiting a tumor selected from the group consisting of prostate cancer and breast cancer, said method comprising:
   administrating a downregulator of TAK1 gene or protein in combination with a chemotherapeutic agent to a patient in need thereof, wherein said downregulator is a small molecular compound that specifically inhibits TAK1 and is selected from the group consisting of 5z-7-oxozeaenol and LYTAK1, and wherein said chemotherapeutic agent is selected from the group consisting of mitoxantrone and bleomycin.

2. The method according to claim 1, characterized in that the tumor is a TAK1 expressing tumor.

3. The method according to claim 1, characterized in that the administration ratio of downregulator of TAK1 gene or protein and the chemotherapeutic agent is 10:0.2.

4. The method according to claim 1, characterized in that when 0.6 mg mitoxantrone is administrated, the corresponding amount of LYTAK1 is 15 mg.

5. The method according to claim 1, characterized in that when 0.3 mg bleomycin is administrated, the corresponding amount of LYTAK1 is 15 mg.

* * * * *